United States Patent
Murakami

(10) Patent No.: US 8,867,314 B2
(45) Date of Patent: Oct. 21, 2014

(54) ULTRASONIC PROBE DEVICE AND ITS CONTROL METHOD

(71) Applicant: Olympus Corporation, Tokyo (JP)

(72) Inventor: Miyuki Murakami, Hachioji (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/774,301

(22) Filed: Feb. 22, 2013

(65) Prior Publication Data

US 2013/0163383 A1 Jun. 27, 2013

Related U.S. Application Data

(63) Continuation of application No. PCT/JP2011/074832, filed on Oct. 27, 2011.

(30) Foreign Application Priority Data

Oct. 27, 2010 (JP) ................................ 2010-240786

(51) Int. Cl.
*H04B 11/00* (2006.01)
*B06B 1/02* (2006.01)
*G01N 29/34* (2006.01)
*G01N 29/24* (2006.01)
*A61B 8/00* (2006.01)

(52) U.S. Cl.
CPC .............. *H04B 11/00* (2013.01); *B06B 1/0292* (2013.01); *G01N 29/348* (2013.01); *A61B 8/4483* (2013.01); *B06B 1/0276* (2013.01); *G01N 29/2406* (2013.01)
USPC .......................................................... 367/137

(58) Field of Classification Search
CPC .... B06B 1/0276; B06B 1/0292; H04B 11/00; A61B 8/4483; G01N 29/348; G01N 29/2406
USPC .................................................. 367/137, 181
See application file for complete search history.

(56) References Cited

U.S. PATENT DOCUMENTS 7,883,466 B2 * 2/2011 Adachi et al. ................. 600/437
2003/0028109 A1 2/2003 Miller (Continued)

FOREIGN PATENT DOCUMENTS

JP H08-229036 A 9/1996
JP 2000-60850 A 2/2000

(Continued)

OTHER PUBLICATIONS

International Preliminary Report on Patentability together with the Written Opinion dated May 23, 2013 received in related International Application No. PCT/JP2011/074832.

(Continued)

*Primary Examiner* — Daniel Pihulic
(74) *Attorney, Agent, or Firm* — Scully, Scott, Murphy & Presser, P.C.

(57) ABSTRACT

An ultrasonic probe device includes capacitive micromachined ultrasonic transducers, a band control unit and a bias voltage change unit. Each of the transducers belongs to one of groups, each of the groups includes at least one of the transducers. The band control unit determines the bias voltage value which varies for each of the groups, and a timing to apply the direct-current bias voltage having the bias voltage value so that all frequencies included in an operating frequency are transmitted and/or received by the ultrasonic probe device during an operation period. The bias voltage change unit changes the direct-current bias voltage to be applied to the capacitive micromachined ultrasonic transducers in accordance with the bias voltage value and the timing.

28 Claims, 12 Drawing Sheets

(56) References Cited

U.S. PATENT DOCUMENTS

| | | | |
|---|---|---|---|
| 2007/0083119 A1* | 4/2007 | Adachi et al. | 600/437 |
| 2013/0163383 A1* | 6/2013 | Murakami | 367/137 |

FOREIGN PATENT DOCUMENTS

| | | |
|---|---|---|
| JP | 2004-222827 A | 8/2004 |
| JP | 2005-510264 A | 4/2005 |
| JP | 2005-349003 A | 12/2005 |
| JP | 2006-122344 A | 5/2006 |
| JP | 2006-200976 A | 8/2006 |
| JP | 2008-119318 A | 5/2008 |
| JP | 2009-055474 A | 3/2009 |
| JP | 2010-232971 A | 10/2010 |
| WO | WO 2005/120355 A1 | 12/2005 |
| WO | WO 2005/120360 A1 | 12/2005 |
| WO | WO 2009/075280 A1 | 6/2009 |

OTHER PUBLICATIONS

International Search Report dated Dec. 13, 2011 issued in PCT/JP2011/074832.

Japanese Office Action dated Jul. 15, 2014 issued in Japanese Patent Application No. 2010-240786.

* cited by examiner

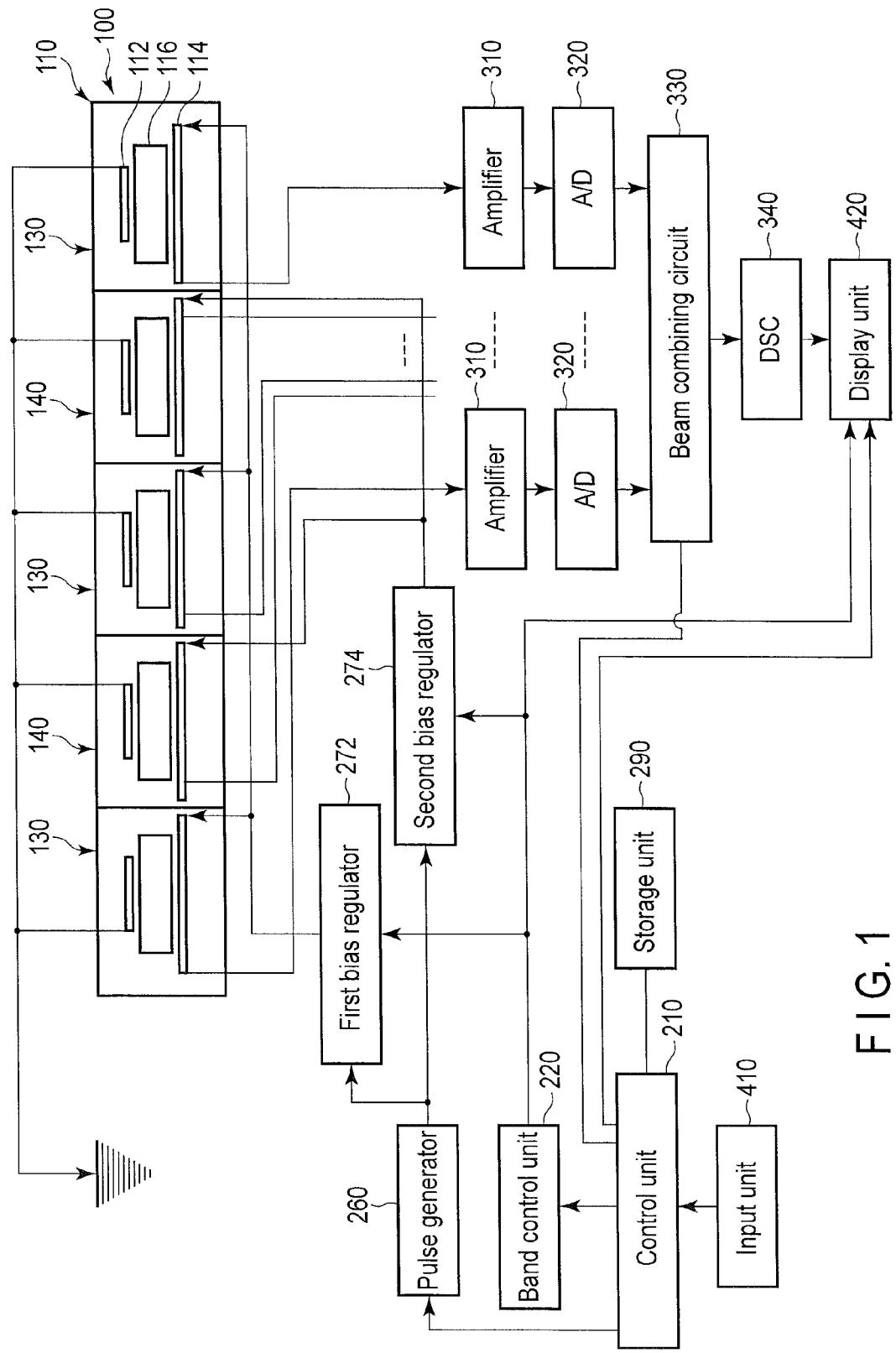
F I G. 1

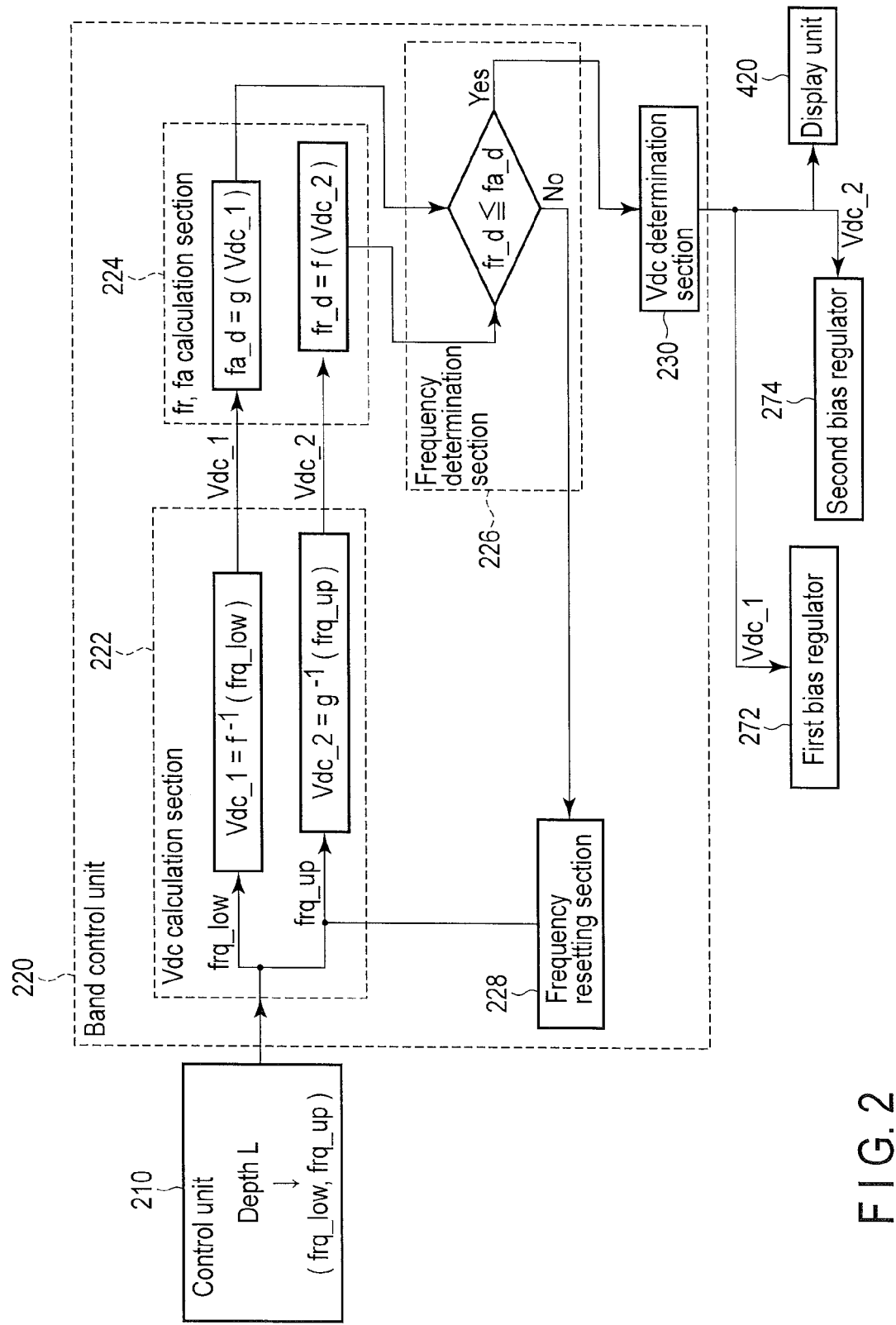
F I G. 2

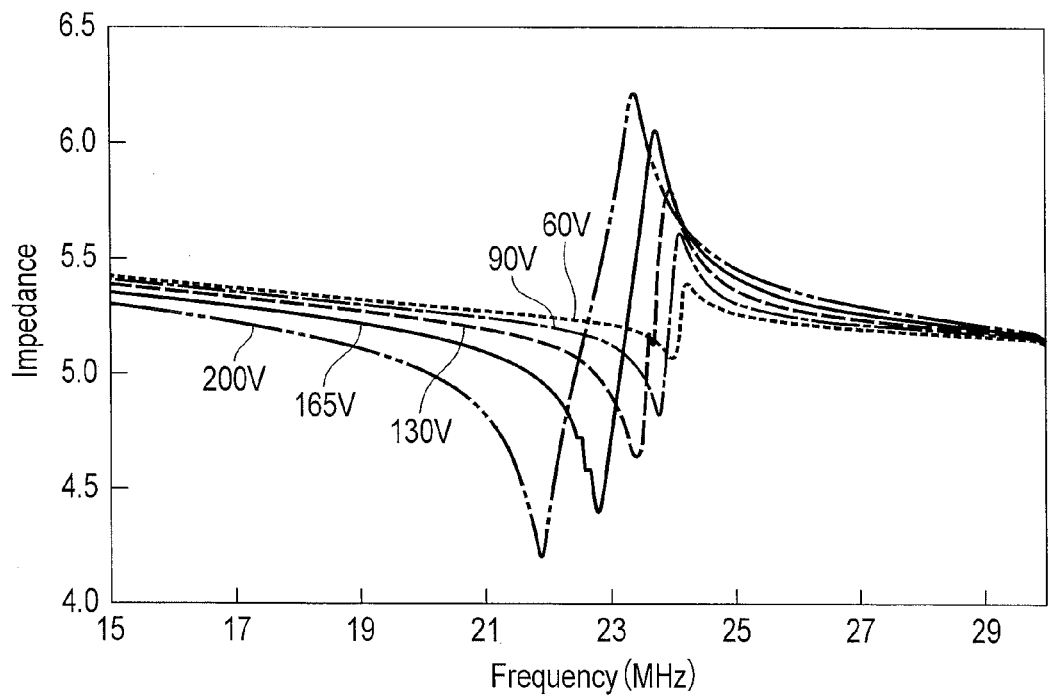
F I G. 3
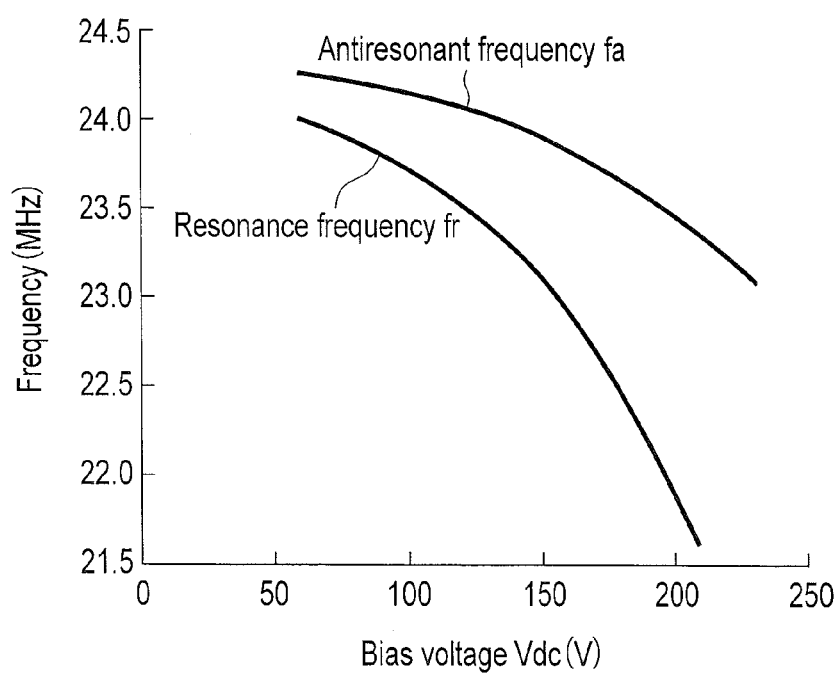
F I G. 4

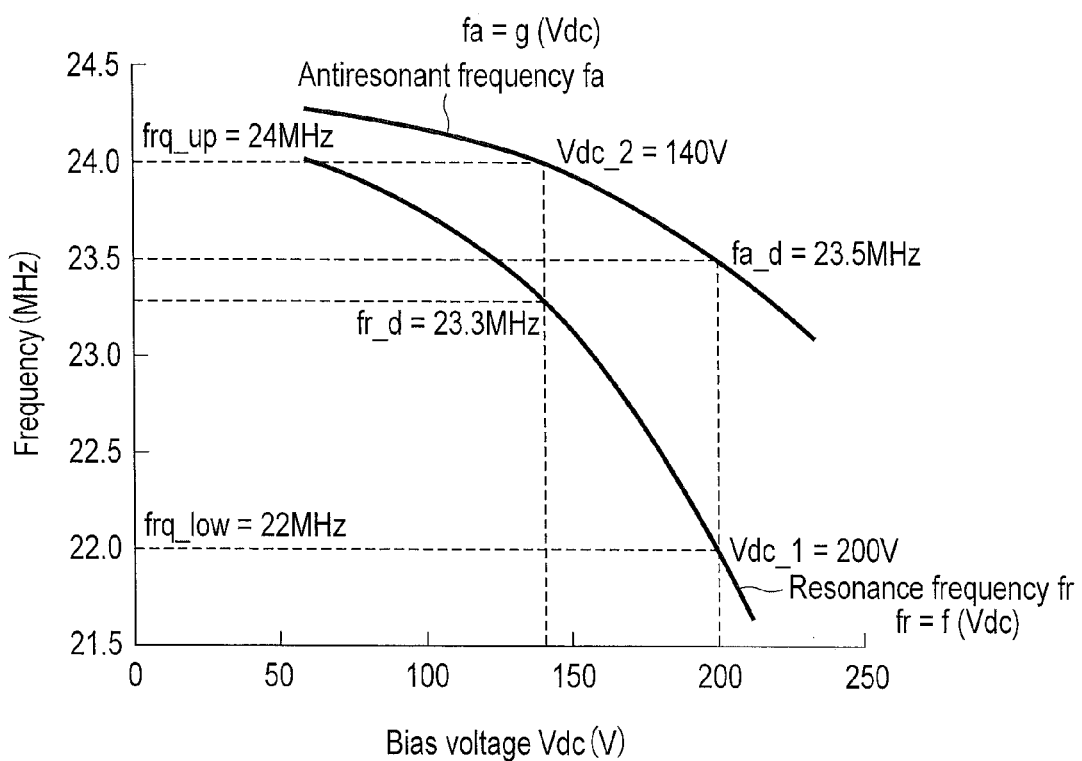
F I G. 5

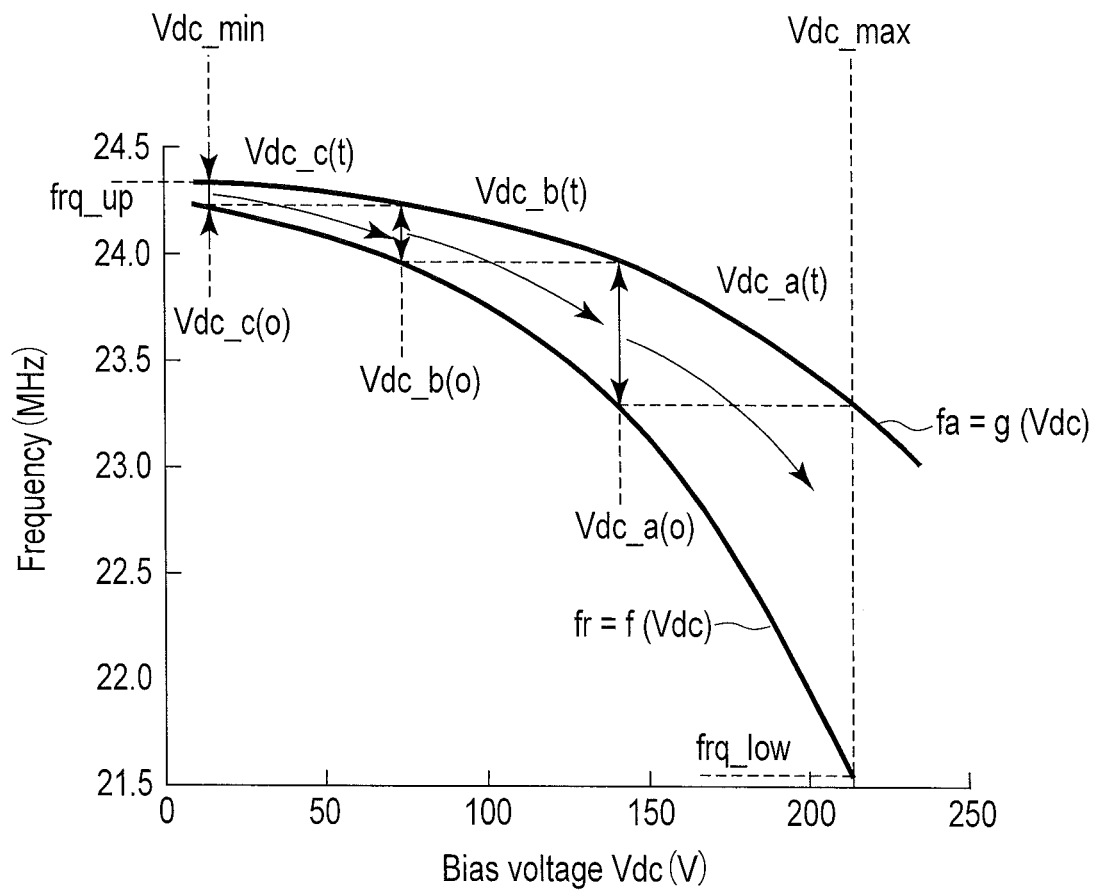
F I G. 10

ULTRASONIC PROBE DEVICE AND ITS CONTROL METHOD

CROSS REFERENCE TO RELATED APPLICATIONS

This application is a Continuation Application of PCT Application No. PCT/JP2011/074832, filed Oct. 27, 2011 and based upon and claiming the benefit of priority from prior Japanese Patent Application No. 2010-240786, filed Oct. 27, 2010, the entire contents of all of which are incorporated herein by reference.

BACKGROUND OF THE INVENTION

1. Field of the Invention

The present invention relates to an ultrasonic probe device, particularly an ultrasonic probe device having a capacitive micromachined ultrasonic transducer, and a control method thereof.

2. Description of the Related Art

In recent years, as ultrasonic elements, much attention is paid to capacitive micromachined ultrasonic transducers (cMUTs). In general, each cMUT includes a lower electrode disposed on a substrate, an upper electrode disposed in a thin film which faces the lower electrode, and a cavity placed between the lower electrode and the upper electrode. When a voltage is applied between the lower electrode and the upper electrode, a capacitance changes between these electrodes, so that the thin film vibrates. By this vibration, the cMUT emits an ultrasonic wave. That is, the cMUT can transmit the ultrasonic wave. Furthermore, when the cMUT receives the ultrasonic wave, the thin film vibrates. By this vibration, charges electrized on the lower electrode and the upper electrode change. By detecting the change of the charges, the cMUT can detect the ultrasonic wave. That is, the cMUT can receive the ultrasonic wave. To allow the cMUT to transmit and receive the ultrasonic wave mentioned above, it is necessary to apply a DC bias voltage between the lower electrode and the upper electrode to beforehand electrize these electrodes. This fact is disclosed in, for example, Jpn. PCT National Publication No. 2005-510264.

An ultrasonic probe device is known in which an ultrasonic image is obtained by transmitting the ultrasonic wave from such a cMUT as mentioned and receiving its reflected wave in the cMUT. In the acquisition of the ultrasonic image by use of such a cMUT, a technique to improve a receiving efficiency of the ultrasonic wave is disclosed in, for example, Jpn. Pat. Appln. KOKAI Publication No. 2006-122344. In the ultrasonic wave which travels through a short distance, an amplitude at the reception is sufficiently large. In consideration of this fact, in the technique disclosed in Jpn. Pat. Appln. KOKAI Publication No. 2006-122344, the DC bias voltage to be applied is set to be low, when the ultrasonic wave reflected in the vicinity of the cMUT is received by the cMUT. The ultrasonic wave which travels through a long distance has small amplitude at the reception, and hence detection sensitivity is low when the DC bias voltage is low. In consideration of this fact, when the ultrasonic wave reflected at a position distant from the cMUT is received by the cMUT, the DC bias voltage to be applied is set to be high, to increase the sensitivity to the ultrasonic wave. Furthermore, in Jpn. Pat. Appln. KOKAI Publication No. 2006-122344, it is disclosed that the DC bias voltage is gradually increased to continuously receive the ultrasonic wave reflected at the near position and the ultrasonic wave reflected at the distant position.

BRIEF SUMMARY OF THE INVENTION

According to an aspect of the present invention, an ultrasonic probe device includes capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of groups, each of the groups including at least one of the capacitive micromachined ultrasonic transducers, a band control unit configured to determine the bias voltage value which varies for each of the groups, and a timing to apply the direct-current bias voltage having the bias voltage value so that all frequencies included in an operating frequency which is a continuous frequency band are transmitted and/or received by the ultrasonic probe device during an operation period of the ultrasonic probe device; and a bias voltage change unit configured to change the direct-current bias voltage to be applied to the capacitive micromachined ultrasonic transducers in accordance with the bias voltage value and the timing determined by the band control unit.

According to an aspect of the present invention, a control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of m (m is a natural number of 2 or more) groups, each of the m groups including at least one of the capacitive micromachined ultrasonic transducers includes calculating a first bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage, when n (n is a natural number of m or less) is 1; determining an n-th bias voltage value so that the minimum value of the transmittable/receivable frequency at the application of the direct-current bias voltage having the n-th bias voltage value is less than or equal to a maximum value of the transmittable/receivable frequency at the application of the direct-current bias voltage having an (n−1)-th bias voltage value, based on the bias voltage-frequency relation information, when n is 2 or more; and applying the direct-current bias voltage having the n-th bias voltage value to the capacitive micromachined ultrasonic transducer belonging to the n-th group.

According to another aspect of the present invention, a control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of m (m is a natural number of 2 or more) groups, each of the m groups including at least one of the capacitive micromachined ultrasonic transducers includes calculating a first bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage; determining a second bias voltage value so that the minimum value of the transmittable/receivable frequency at application of the direct-current bias voltage having the second bias voltage value is less than or equal to a maximum value of the transmittable/receivable frequency at application of the direct-current bias voltage having the first bias voltage value, based on the bias voltage-frequency relation information; changing a first applied bias voltage value from the second bias voltage value to the first bias voltage value, with an elapse of time during an operation period, the first applied bias voltage value being a value of an n-th applied bias voltage value (n is a natural number of m or less) when n is 1, the n-th applied bias voltage value being the bias voltage value of the direct-current bias voltage to be applied to the capacitive micromachined ultrasonic transducer belonging to an n-th group; determining the n-th applied bias voltage value so that the minimum value of the transmittable/receivable frequency at application of the direct-current bias voltage having the n-th applied bias voltage value is less than or equal to the maximum value of the transmittable/receivable frequency at application of the direct-current bias voltage having an (n−1)-th applied bias voltage value, based on the bias voltage-frequency relation information, when n is 2 or more; and applying the direct-current bias voltage having the n-th applied bias voltage value to the capacitive micromachined ultrasonic transducer belonging to the n-th group.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a block diagram showing a configuration example of an ultrasonic probe device according to a first embodiment of the present invention;

FIG. 2 is a block diagram showing a configuration example of a part concerned with determination of a bias voltage to be applied to each cMUT of the ultrasonic probe device according to the first embodiment of the present invention;

FIG. 3 is a diagram showing an example of frequency characteristics of impedance in accordance with the bias voltage to be applied, in the cMUT;

FIG. 4 is a diagram showing an example of a relation between the bias voltage to be applied and a resonance frequency and an example of a relation between the bias voltage to be applied and an antiresonant frequency in the cMUT;

FIG. 5 is a diagram for explaining an example of a method of determining the bias voltage to be applied to the cMUT of the ultrasonic probe device according to the first embodiment of the present invention;

FIG. 10 is a diagram for explaining an example of the bias voltage to be applied to the cMUT of the ultrasonic probe device according to a modification of the second embodiment of the present invention;

DETAILED DESCRIPTION OF THE INVENTION

First Embodiment

Figure 6:
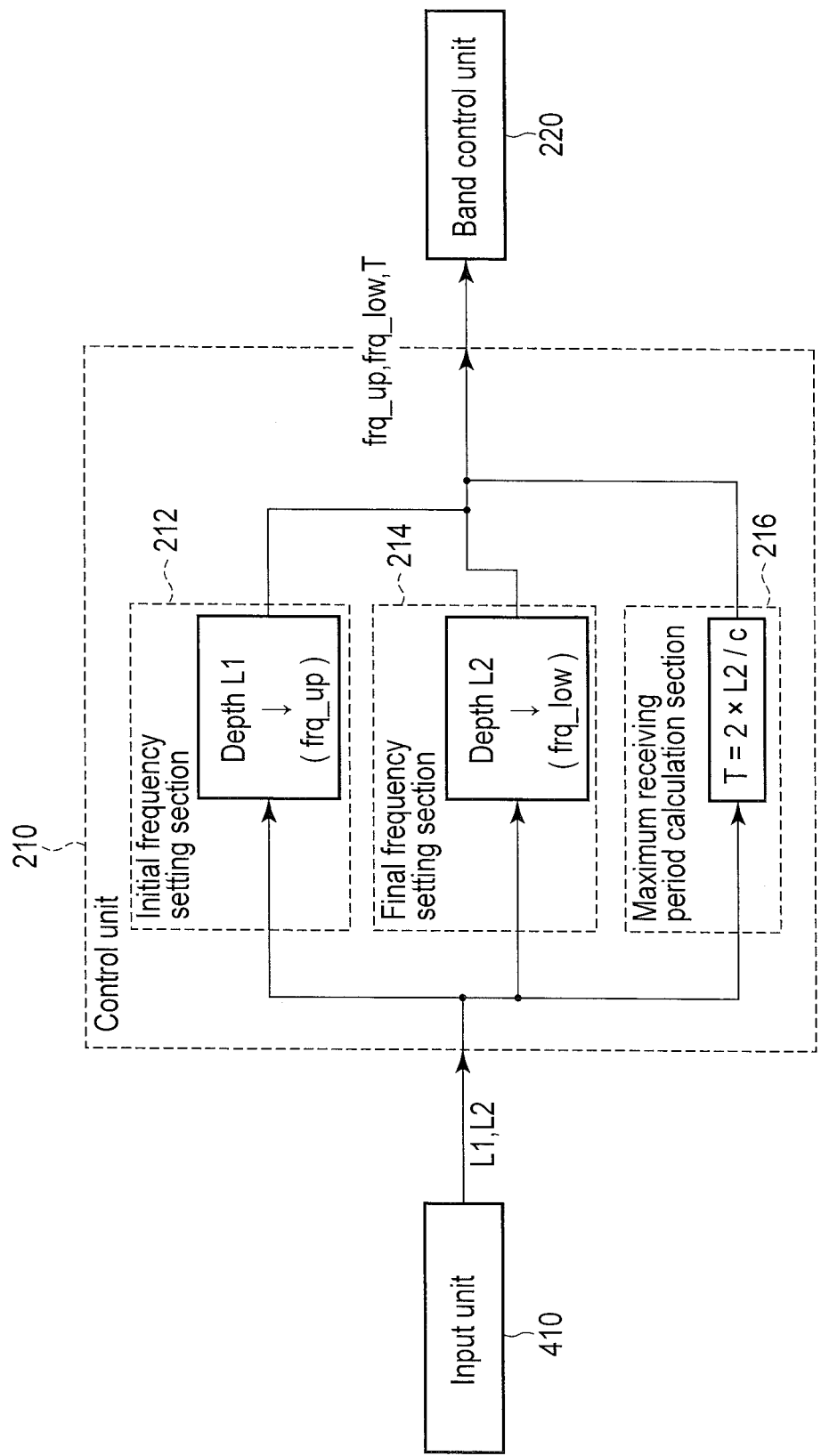
FIG. 6 is a block diagram showing a configuration example of a part concerned with determination of a bias voltage to be applied to each cMUT of an ultrasonic probe device according to a second embodiment of the present invention.

A first embodiment of the present invention will be described with reference to the drawings. A configuration of an ultrasonic probe device according to the present embodiment is schematically shown in FIG. 1. In the present ultrasonic probe device, capacitive micromachined ultrasonic transducers (cMUTs) are used as ultrasonic sources. The present ultrasonic probe device comprises a cMUT array 100 including cMUTs 110. In the cMUT array 100, the cMUTs 110 are arranged in a planar manner in an emitting direction of aligned ultrasonic waves.

Each of the cMUTs 110 includes an upper electrode 112 and a lower electrode 114, the electrodes facing each other. A cavity 116 is placed between the upper electrode 112 and the lower electrode 114. When AC voltage is applied between the upper electrode 112 and the lower electrode 114 in each of the cMUTs 110, capacitance between the electrodes changes, and electrostatic attractive force between the electrodes changes. The lower electrode 114 and a peripheral structure of the electrode are made immobile, and hence owing to the change of the electrostatic attractive force, the upper electrode 112 and a peripheral structure of the upper electrode vibrate. Therefore, each of the cMUTs 110 generates an ultrasonic wave when the AC voltage is applied between the upper electrode 112 and the lower electrode 114. In this way, the cMUT 110 can transmit the ultrasonic wave.

Moreover, when the ultrasonic wave enters each of the cMUTs 110, the upper electrode 112 and the peripheral structure vibrate. As a result, the capacitance changes between the upper electrode 112 and the lower electrode 114. The entrance of the ultrasonic wave can be detected by measuring this change of the capacitance between the upper electrode 112 and the lower electrode 114. In this way, the cMUT 110 can receive the ultrasonic wave. The ultrasonic probe device uses such an ultrasonic transmitting/receiving function of the cMUT 110 to acquire an internal image of an object by the ultrasonic wave.

In the cMUT 110, when a bias voltage is beforehand applied between the upper electrode 112 and the lower electrode 114, frequency characteristics of the vibration of the upper electrode 112 change. The higher the applied bias voltage is, the lower a resonance frequency of the upper electrode 112 becomes. Therefore, when the applied bias voltage is higher, the cMUT 110 can emit the ultrasonic wave of the lower frequency, and receive the ultrasonic wave of the lower frequency. Conversely, the lower the applied bias voltage is, the higher the resonance frequency of the upper electrode 112 becomes. Therefore, when the applied bias voltage is lower, the cMUT 110 can emit the ultrasonic wave of the higher frequency, and receive the ultrasonic wave of the higher frequency.

In the present embodiment, the cMUTs 110 which belong to the cMUT array 100 are divided into two groups. That is, the cMUT array 100 includes the cMUTs 110 forming a first group, and the cMUTs 110 forming a second group. A high bias voltage is applied to the cMUTs 110 of the first group, and a low bias voltage is applied to the cMUTs 110 of the second group. In consequence, the whole cMUT array 100 regarded as one transmitting/receiving unit can expand a frequency band of the ultrasonic waves which can be transmitted and received. Hereinafter, the cMUTs 110 of the first group will be referred to as first cMUTs 130, and the cMUTs 110 of the second group will be referred to as second cMUTs 140.

For allowing the cMUT array 100 to emit the ultrasonic waves, the present ultrasonic probe device includes a control unit 210, a band control unit 220, a pulse generator 260, a first bias regulator 272, a second bias regulator 274, and a storage unit 290. Moreover, for allowing the cMUT array 100 to detect the ultrasonic waves, the present ultrasonic probe device includes amplifiers 310, A/D converters 320, a beam combining circuit 330, and a digital scan converter (DSC) 340. Furthermore, the present ultrasonic probe device includes an input unit 410 and a display unit 420.

The input unit 410 is, for example, a keyboard connected to the control unit 210. A user uses this keyboard to input information on a depth (the desirable depth) of a portion from which an image is to be acquired. The input depth information is output to the control unit 210. The control unit 210 determines the frequency band of the ultrasonic waves emitted by the cMUT array 100 on the basis of the input depth information, and outputs values concerned with the frequency band to the band control unit 220. Moreover, the control unit 210 controls the pulse generator 260. Furthermore, the control unit 210 controls the whole present ultrasonic probe device.

Therefore, the control unit 210 is also connected to, for example, the beam combining circuit 330. Additionally, the control unit 210 is also connected to the storage section 290. Consequently, when the control unit 210 controls each section of the present ultrasonic probe device, the control unit 210 can suitably use the information stored in the storage section 290. Moreover, the control unit 210 is connected to the display unit 420, and enables the display unit 420 to display necessary information.

Into the band control unit 220, the values concerned with the frequency band are input from the control unit 210. On the basis of the input values, the band control unit 220 calculates two bias regulation values. These two bias regulation values are required to satisfy the frequency band of the ultrasonic waves emitted by the cMUT array 100 at a time when the image at the desirable depth is acquired. The band control unit 220 outputs one (the first bias regulation value) of the two calculated bias regulation values to the first bias regulator 272, and outputs the other (second) bias regulation value to the second bias regulator 274. Moreover, the band control unit 220 outputs the two bias regulation values to the display unit 420. Additionally, the band control unit 220 is also connected to the storage section 290 via the control unit 210. Therefore, the band control unit 220 can suitably read the information stored in the storage section 290, and use the read information.

The pulse generator 260 under the control of the control unit 210 generates pulse signals, and outputs the signals to the first bias regulator 272 and the second bias regulator 274. Into the first bias regulator 272, the first bias regulation value is input from the band control unit 220, and the pulse signal is also input from the pulse generator 260. Then, the first bias regulator 272 outputs a drive signal to each of the first cMUTs 130. This drive signal is a signal obtained by superimposing the pulse signal on the bias voltage regulated on the basis of the first bias regulation value. On the other hand, into the second bias regulator 274, the second bias regulation value is input from the band control unit 220, and the pulse signal is input from the pulse generator 260. Then, the second bias regulator 274 also outputs a drive signal to each of the second cMUTs 140 similarly to the first bias regulator 272. This drive signal is a signal obtained by superimposing the pulse signal on the bias voltage regulated on the basis of the second bias regulation value. In this way, for example, the first bias regulator 272 and the second bias regulator 274 function as bias voltage change units. Additionally, a signal line from the band control unit 220 to the display unit 420, a signal line from the band control unit 220 to the first bias regulator 272 and a signal line from the band control unit 220 to the second bias regulator 274 may be separate signal lines from the beginning.

Each of the amplifiers 310 is connected to the one cMUT 110. Into the amplifier 310, a potential difference between the upper electrode 112 and the lower electrode 114 of each of the cMUTs 110 is input as an output signal of the cMUT 110, and the amplifier 310 amplifies the output signal. The amplifier 310 outputs the amplified signal to each of the A/D converters 320. Into the A/D converter 320, the amplified signal is input from the amplifier 310. The A/D converter 320 performs A/D conversion of the input signal, and outputs, to the beam combining circuit 330, a digital signal obtained by the conversion (hereinafter referred to as the digital echo signal).

Into the beam combining circuit 330, the digital echo signals are input from the respective A/D converters 320. The beam combining circuit 330 combines the digital echo signals input from the A/D converters 320, to generate image signals. The beam combining circuit 330 outputs the generated image signals to the control unit 210 and the DSC 340. Into the DSC 340, the image signal is input from the beam combining circuit 330. The DSC 340 prepares a signal for display on the basis of the image signal input from the beam combining circuit 330. This signal for display is a signal for allowing, for example, the display unit 420 as a monitor to display an image. The DSC 340 outputs the prepared signal for display to the display unit 420. Into the display unit 420, the signal for display is input from the DSC 340. Consequently, the display unit 420 displays the image on the basis of the signal for display. Moreover, into the display unit 420, the bias regulation value is input from the band control unit 220. In consequence, the display unit 420 displays the bias regulation value.

Here, the values to be displayed in the display unit 420 may be any of (1) numeric values of the two bias regulation values themselves, (2) numeric values of the frequency bands of the first cMUTs 130 and second cMUTs 140, (3) numeric values of a frequency band of the first cMUTs 130 combined with the second cMUTs 140, (4) graphical representations of the numeric values, and (5) combinations of the above (1) to (4).

A configuration of the band control unit 220 will further be described with reference to FIG. 2. The band control unit 220 includes a Vdc calculation section 222, an fr and fa calculation section 224, a frequency determination section 226, a frequency resetting section 228, and a Vdc determination section 230 as shown in FIG. 2. The values concerned with the frequency band are input from the control unit 210 into the Vdc calculation section 222. The Vdc calculation section 222, the fr and fa calculation section 224, the frequency determination section 226 and the frequency resetting section 228 perform predetermined operations to calculate the bias regulation values, and the Vdc determination section 230 determines the bias regulation values. The Vdc determination section 230 outputs the determined bias regulation values to the first bias regulator 272, the second bias regulator 274, and the display unit 420. Details of the respective sections in the band control unit 220 will be described later together with explanation of an operation of the ultrasonic probe device according to the present embodiment.

The operation of the ultrasonic probe device according to the present embodiment will be described with reference to the drawings. First, the emission of the ultrasonic wave according to the present embodiment will be described. The input unit 410 acquires, from the user, for example, a distance between the cMUT array 100 and the most distant position of the portion from which the image is to be acquired, i.e., a depth L of the deepest portion of the portion from which the image is to be acquired. The input unit 410 is, for example, the keyboard into which the user inputs a value of the depth L. The input unit 410 outputs the acquired value of the depth L to the control unit 210.

Moreover, the input unit 410 is not limited to the keyboard, and may use a button, a lever, a knob or the like as long as the value of the depth L can be input. Furthermore, the input unit 410 may be a mouse. In this case, by use of the mouse, the user can select the value of the depth L from the image displayed in the display unit 420, or select the button indicating increase or decrease to determine the value of the depth L. Moreover, the user can determine the value of the depth L which is associated with the image by selecting a part of the image displayed in the display unit 420. In these cases, the control unit 210, the input unit 410 which is the mouse and the display unit 420 cooperate to acquire the value of the depth L.

The control unit 210 which has acquired the value of the depth L determines a minimum value frq_low and a maximum value frq_up on the basis of the value of the depth L. The minimum value frq_low and the maximum value frq_up are the above-mentioned values concerned with the frequency band, and the values represent the frequency band where the cMUT array 100 functions. The control unit 210 outputs the determined minimum value frq_low and maximum value frq_up to the Vdc calculation section 222 in the band control unit 220.

Here, the control unit 210 uses, for example, the following method, to determine the minimum value frq_low and the maximum value frq_up from the value of the depth L. For example, a relation between the depth L and each of the minimum value frq_low and the maximum value frq_up may be stored as a table in the storage unit 290, and the control unit 210 may determine the minimum value frq_low and the maximum value frq_up from the value of the depth L on the basis of the relation stored in the storage unit 290. Moreover, the storage unit 290 may store an equation indicating the relation between the depth L and each of the minimum value frq_low and the maximum value frq_up, and the control unit 210 may calculate the minimum value frq_low and the maximum value frq_up from the value of the depth L in accordance with the equation. In this way, the storage unit 290 functions as the storage unit concerning the distance (the depth)–the frequency.

The minimum value frq_low and the maximum value frq_up output from the control unit 210 are input into the Vdc calculation section 222 of the band control unit 220. The Vdc calculation section 222 calculates a first bias voltage value Vdc_1 on the basis of the minimum value frq_low, and calculates a second bias voltage value Vdc_2 on the basis of the maximum value frq_up.

Here, the calculation of the first bias voltage value Vdc_1 and the second bias voltage value Vdc_2 will be described with reference to the drawing. FIG. 3 shows an example of a relation (characteristics) between a vibration frequency and electric impedance in the cMUTs 110. In FIG. 3, the horizontal axis shows the frequency, and the vertical axis shows the impedance. Also in FIG. 3, a dotted line, a dashed-dotted line, a broken line, a solid line and a dashed-two-dotted line show the characteristics at a time when a bias voltage to be applied between the upper electrode 112 and the lower electrode 114 (hereinafter referred to simply as the bias voltage) is 60 V, 90 V, 130 V, 165 V, and 200 V, respectively. As shown in FIG. 3, even at the different bias voltages, the whole tendencies of the frequency and the impedance are similar. That is, the impedance of each of the cMUTs 110 gradually decreases to take the minimal value, increases to take the maximal value, and then decreases again, as the frequency increases.

Here, the frequency at which the impedance takes the minimal value is a resonance frequency of the corresponding cMUT 110, and the frequency at which the impedance takes the maximal value is an antiresonant frequency of the cMUT 110. The frequency band where each of the cMUTs 110 functions is frequencies from the resonance frequency to the antiresonant frequency mentioned here.

As shown in FIG. 3, when the bias voltage varies, the resonance frequency and the antiresonant frequency also vary. More specifically, the higher the bias voltage is, the lower the resonance frequency and antiresonant frequency of the cMUT 110 become. The lower the bias voltage is, the higher the frequencies become. Therefore, the higher the bias voltage is, the lower the frequency band where the cMUT 110 functions becomes. The lower the bias voltage is, the higher the frequency band becomes.

FIG. 4 shows an example of a relation between a bias voltage Vdc_and a resonance frequency fr, and an example of a relation between the bias voltage Vdc_and an antiresonant frequency fa. As shown in the drawing, in accordance with the characteristics of the cMUT 110, the relation between the bias voltage Vdc_and the resonance frequency fr is represented by a function f as follows:

$$fr = f(Vdc). \quad (1)$$

Moreover, in accordance with the characteristics of the cMUT 110, the relation between the bias voltage Vdc_and the antiresonant frequency fa is represented by a function g as follows:

$$fa = g(Vdc). \quad (2)$$

In the present embodiment, the above equations (1) and (2) are stored in the storage unit 290, and the band control unit 220 can read the above equations (1) and (2) via the control unit 210.

The operation according to the present embodiment will be described with reference to FIG. 2 again. In the present embodiment, the Vdc calculation section 222 calculates the first bias voltage value Vdc_1 by use of the equation (1) and the minimum value frq_low input from the control unit 210 in accordance with the following equation (3):

$$Vdc\_1 = f^{-1}(\text{frq\_low}). \quad (3)$$

Similarly, the Vdc calculation section 222 calculates the second bias voltage value Vdc_2 by use of the equation (2) and the maximum value frq_up input from the control unit 210 in accordance with the following equation (4):

$$Vdc\_2 = g^{-1}(\text{frq\_up}). \quad (4)$$

The Vdc calculation section 222 outputs the calculated first bias voltage value Vdc_1 and second bias voltage value Vdc_2 to the fr and fa calculation section 224.

The first bias voltage value Vdc_1 and the second bias voltage value Vdc_2 are input from the Vdc calculation section 222 into the fr and fa calculation section 224. The fr and fa calculation section 224 calculates an antiresonant frequency fa_d for determination by use of the first bias voltage value Vdc_1 and the equation (2) in accordance with the following equation (5):

$$fa\_d = g(Vdc\_1). \quad (5)$$

Similarly, the fr and fa calculation section 224 calculates a resonance frequency fr_d for determination by use of the second bias voltage value Vdc_2 and the equation (1) in accordance with the following equation (6):

$$fr\_d = f(Vdc\_2). \quad (6)$$

The fr and fa calculation section 224 outputs, to the frequency determination section 226, the calculated resonance frequency fr_d for determination, the calculated antiresonant frequency fa_d for determination, the first bias voltage value Vdc_1 and the second bias voltage value Vdc_2.

The frequency determination section 226 determines whether or not the resonance frequency fr_d for determination and antiresonant frequency fa_d for determination input from the Vdc calculation section 222 have a relation of fr_d≤fa_d. When fr_d≤fa_d is true, the frequency determination section 226 outputs, to the Vdc determination section 230, the first bias voltage value Vdc_1 and second bias voltage value Vdc_2 input from the fr and fa calculation section 224.

On the other hand, when fr_d≤fa_d is false, the frequency determination section 226 outputs, to the frequency resetting section 228, a signal indicating that fr_d≤fa_d is false. The frequency resetting section 228 into which the signal indicating that fr_d≤fa_d is false has been input from the frequency determination section 226 acquires the maximum value frq_up from the Vdc calculation section 222, and sets, to a new maximum value frq_up, a value which is smaller than the acquired maximum value frq_up as much as a predetermined value. The frequency resetting section 228 outputs the reset new maximum value frq_up to the Vdc calculation section 222. The Vdc calculation section 222 into which the new maximum value frq_up has been input from the frequency resetting section 228 similarly determines the first bias voltage value Vdc_1 and the second bias voltage value Vdc_2, and outputs these values to the fr and fa calculation section 224 as described above. Now, processing is similarly advanced as described above. In this case, the first bias voltage value Vdc_1 and the antiresonant frequency fa_d for determination do not change. Therefore, the Vdc calculation section 222 does not have to again calculate the first bias voltage value Vdc_1, and may only hold the previously calculated first bias voltage value Vdc_1. Similarly, the fr and fa calculation section 224 does not have to again calculate the antiresonant frequency fa_d for determination, and may only hold the previously calculated antiresonant frequency fa_d for determination.

As described above, the frequency resetting section 228 repeats resetting processing to decrease the maximum value frq_up until the frequency determination section 226 determines that fr_d≤fa_d is true. When fr_d≤fa_d is true, the frequency determination section 226 outputs the first bias voltage value Vdc_1 and the second bias voltage value Vdc_2 to the Vdc determination section 230.

When fr_d≤fa_d is true, the first bias voltage value Vdc_1 and the second bias voltage value Vdc_2 are input into the Vdc determination section 230 from the frequency determination section 226. The Vdc determination section 230 determines that the bias voltage to be applied to the first cMUTs 130 is the first bias voltage value Vdc_1 and that the bias voltage to be applied to the second cMUTs 140 is the second bias voltage value Vdc_2. The Vdc determination section 230 outputs the first bias voltage value Vdc_1 to the first bias regulator 272, and outputs the second bias voltage value Vdc_2 to the second bias regulator 274. Moreover, the Vdc determination section 230 outputs signals indicating the first bias voltage value Vdc_1 and the second bias voltage value Vdc_2 to the display unit 420.

The first bias regulator 272 applies, to the first cMUTs 130, the first bias voltage value Vdc_1 input from the Vdc determination section 230. Similarly, the second bias regulator 274 applies, to the second cMUTs 140, the second bias voltage value Vdc_2 input from the Vdc determination section 230. The display unit 420 displays values of the first bias voltage value Vdc_1 and the second bias voltage value Vdc_2. In this case, the values are not limited to the first bias voltage value Vdc_1 and the second bias voltage value Vdc_2, and the minimum value frq_low and the antiresonant frequency fa_d for determination as well as the resonance frequency fr_d for determination and the maximum value frq_up may be displayed in the display unit 420.

In this way, for example, the Vdc calculation section 222 functions as a bias voltage calculation section, and, for example, the fr and fa calculation section 224 functions as a frequency calculation section.

Here, relations among the minimum value frq_low and the maximum value frq_up, the resonance frequency fr_d for determination and the antiresonant frequency fa_d for determination, and the first bias voltage value Vdc_1 and the second bias voltage value Vdc_2 will be described with reference to an example shown in FIG. 5. In the example shown in FIG. 5, the minimum value frq_low is 22 MHz, and the maximum value frq_up is 24 MHz.

In this case, the first bias voltage value Vdc_1 of 200 V is obtained from the minimum value frq_low=22 MHz by use of the above equation (3). At this time, the antiresonant frequency fa_d for determination of 23.5 MHz is obtained by using the above equation (5). On the other hand, the second bias voltage value Vdc_2 of 140 V is obtained from the maximum value frq_up=24 MHz by use of the above equation (4). At this time, the resonance frequency fr_d for determination of 23.3 MHz is obtained by using the above equation (6). Since fr_d=23.3 MHz fa_d=23.5 MHz, the frequency determination section 226 outputs the first bias voltage value Vdc_1 and the second bias voltage value Vdc_2 to the Vdc determination section 230.

In the example shown in FIG. 5, the first cMUTs 130 to which the first bias voltage value Vdc_1=200 V is applied function from the minimum value frq_low=22 MHz which is the resonance frequency to the antiresonant frequency fa_d for determination=23.5 MHz which is the antiresonant frequency. Moreover, the second cMUTs 140 to which the second bias voltage value Vdc_2=140 V is applied function from the resonance frequency fr_d for determination=23.3 MHz which is the resonance frequency to the maximum value frq_up=24 MHz which is the antiresonant frequency. Therefore, the cMUT array 100 including the first cMUTs 130 and the second cMUTs 140 functions (can transmit and receive the ultrasonic waves) in a frequency band of 22 MHz to 24 MHz.

As above, when fr_d≤fa_d is true, the cMUT array 100 can transmit and receive the ultrasonic waves continuously in a frequency band of the minimum value frq_low to the maximum value frq_up without being interrupted. Additionally, when fr_d≤fa_d is false, the frequency band where the cMUT array 100 functions becomes discontinuous, and a frequency band where the array does not function is present between the minimum value frq_low and the maximum value frq_up. In the present embodiment, the determination in the frequency determination section 226 and the resetting of the frequency in the frequency resetting section 228 are performed so that this discontinuous frequency band is not present.

The continuation of the operation of the ultrasonic probe device according to the present embodiment will be described with reference to FIG. 1 again. The first bias regulator 272 applies, to the first cMUTs 130, the first bias voltage value Vdc_1 input from the Vdc determination section 230. Similarly, the second bias regulator 274 applies, to the second cMUTs 140, the second bias voltage value Vdc_2 input from the Vdc determination section 230. The display unit 420 displays values of the first bias voltage value Vdc_1 and the second bias voltage value Vdc_2.

In the acquisition of the ultrasonic image, the control unit 210 outputs, to the pulse generator 260, an instruction to generate pulses. The pulse generator 260 generates the pulses under the control of the control unit 210. The pulse generator 260 outputs the generated pulses to the first bias regulator 272 and the second bias regulator 274. The first bias regulator 272 superimposes the pulse input from the pulse generator 260 on the first bias voltage value Vdc_1, and outputs the superimposed signal to the first cMUTs 130. The second bias regulator 274 superimposes the pulse input from the pulse generator 260 on the second bias voltage value Vdc_2, and outputs the superimposed signal to the second cMUTs 140.

The first cMUTs 130 vibrate in accordance with the superimposed pulse waves, from a state where the first bias voltage value Vdc_1 is applied, to emit ultrasonic waves having frequency components from the minimum value frq_low to the antiresonant frequency fa_d for determination. Similarly, the second cMUTs 140 vibrate in accordance with the superimposed pulse waves, from a state where the second bias voltage value Vdc_2 is applied, to emit ultrasonic waves having frequency components from the resonance frequency fr_d for determination to the maximum value frq_up. As a result, the cMUT array 100 including the first cMUTs 130 and the second cMUTs 140 emits ultrasonic waves having frequency components of a band of the minimum value frq_low to the maximum value frq_up.

The ultrasonic waves emitted from the cMUT array 100 travels through an irradiation object. Part of the traveling ultrasonic waves is reflected in accordance with an acoustic impedance of the irradiation object. Additionally, when the ultrasonic wave traveling through the irradiation object has a higher frequency, the ultrasonic wave easily decays. In consequence, the ultrasonic wave having a lower frequency travels to a position distant from the cMUT array 100. In the present embodiment, the frequency of the ultrasonic wave is selected so that the ultrasonic wave reaches the position corresponding to the depth L. The ultrasonic wave reflected in the irradiation object reaches the cMUT array 100 again. The ultrasonic wave which has reached the cMUT array 100 vibrates the upper electrode 112 of each of the cMUTs 110 of the cMUT array 100. By the vibration of the upper electrode 112, the potential difference between the upper electrode 112 and the lower electrode 114 changes.

Here, since the first bias voltage value Vdc_1 is applied to the first cMUTs 130, the first cMUTs 130 can receive the ultrasonic waves of a band of the minimum value frq_low to the antiresonant frequency fa_d for determination. On the other hand, since the second bias voltage value Vdc_2 is applied to the second cMUTs 140, the second cMUTs 140 can receive the ultrasonic waves of a band of the resonance frequency fr_d for determination to the maximum value frq_up. As a result, the cMUT array 100 can receive the ultrasonic waves having frequency components of the band of the minimum value frq_low to the maximum value frq_up.

In this way, for example, the band of the minimum value frq_low to the maximum value frq_up corresponds to an operating frequency, and, for example, the band of the minimum value frq_low to the antiresonant frequency fa_d for determination in the state where the first bias voltage value Vdc_1 is applied corresponds to a transmittable/receivable frequency in the state where the first bias voltage value Vdc_1 is applied.

The potential difference between the upper electrode 112 and the lower electrode 114 in each of the cMUTs 110 is output to each of the amplifiers 310. The amplifier 310 amplifies the input potential difference, and outputs a signal to each of the A/D converters 320. The A/D converter 320 performs the A/D conversion of the amplified signal input from the amplifier 310, and outputs, to the beam combining circuit 330, the digital echo signal obtained by the conversion.

The digital echo signals are input from the respective A/D converters 320 into the beam combining circuit 330. Then, the beam combining circuit 330 combining the digital echo signals, to form image signals. As a result, the beam combining circuit 330 can acquire the image at the predetermined depth. The beam combining circuit 330 outputs the acquired image signals to the control unit 210 and the DSC 340. On the basis of the image signal input from the beam combining circuit 330, the DSC 340 prepares the signal for display to be displayed in the display unit 420 which is, for example, the monitor. The DSC 340 outputs the prepared signal for display to the display unit 420. The signal for display is input from the DSC 340 into the display unit 420, and the display unit 420 displays the image on the basis of the signal for display.

As described above, the ultrasonic probe device according to the present embodiment can irradiate the ultrasonic irradiation object with the ultrasonic wave, and acquire the image in the ultrasonic irradiation object on the basis of the reflected ultrasonic wave from the ultrasonic irradiation object.

In the present embodiment, the cMUTs 110 of the cMUT array 100 are divided into two groups of the first cMUTs 130 and the second cMUTs 140, and different bias voltages are applied to the groups, respectively. As a result, the first cMUTs 130 and the second cMUTs 140 function in mutually different frequency bands. In addition, the two frequency bands are set so that the bands are adjacent to each other or overlap with each other, i.e., the bands are not away from each other. According to the present embodiment, owing to the combination of the two groups, the ultrasonic probe device can transmit (emit) the ultrasonic waves of high energy over a wide frequency band, and efficiently receive the ultrasonic waves of the wide frequency band. The ultrasonic waves of the wide frequency band can be used in both the transmission (the emission) and the reception, and hence the ultrasonic probe device according to the present embodiment can efficiently acquire an image having a large depth. Moreover, according to the present embodiment, the cMUT array 100 itself functions as a so-called frequency filter, and hence it is not necessary to separately dispose the frequency filter in a receiving circuit or the like, with the result that a circuit configuration can be simplified.

Additionally, it has been described in the present embodiment that the relation between the bias voltage Vdc and the resonance frequency fr and the relation between the bias voltage Vdc and the antiresonant frequency fa are represented by equations such as the above equations (1) and (2), but needless to say, tables indicating these relations may be prepared and used. Further in the present embodiment, there has been described an example where the relation between the bias voltage Vdc_and each of the resonance frequency fr and the antiresonant frequency fa is used as the relation between the bias voltage Vdc_and the frequency at which each of the cMUTs 110 functions. However, it is possible to similarly use a relation indicating the frequency characteristics of the cMUT 110 in accordance with the bias voltage Vdc, for example, a full width at half maximum of amplitude of the vibrating surface of the cMUT 110 to the frequency.

Modification of First Embodiment

A modification of the first embodiment will be described, and the description is limited to differences from the first embodiment. In the first embodiment, the cMUTs 110 of the cMUT array 100 are divided into two groups of the first cMUTs 130 and the second cMUTs 140. In the present modification, the cMUTs 110 of the cMUT array 100 are divided into three groups.

Therefore, the cMUT array 100 includes a first cMUTs, a second cMUTs and a third cMUTs. Moreover, a bias voltage of the first cMUTs is regulated by a first bias regulator, a bias voltage of the second cMUTs is regulated by a second bias regulator, and a bias voltage of the third cMUTs is regulated by a third bias regulator.

Also in the present modification, a control unit 210 acquires a value of a depth L, determines a minimum value frq_low on the basis of the value of the depth L, and outputs the value to a Vdc calculation section 222 in a band control unit 220.

The Vdc calculation section 222 in the band control unit 220 uses the minimum value frq_low as a first resonance frequency fr_1 for determination, and calculates a first bias voltage value Vdc_1 in accordance with $Vdc\_1 = f^{-1}(fr\_1)$ on the basis of the first resonance frequency fr_1 for determination and a function f, similarly to the first embodiment. The Vdc calculation section 222 outputs the calculated first bias voltage value Vdc_1 to an fr and fa calculation section 224.

The fr and fa calculation section 224 calculates a first antiresonant frequency fa_1 for determination in accordance with $fa\_1 = g(Vdc\_1)$ on the basis of the first bias voltage value Vdc_1 and a function g. Differently from the first embodiment, in the present modification, the fr and fa calculation section 224 outputs the calculated first antiresonant frequency fa_1 for determination to the Vdc calculation section 222.

Next, the Vdc calculation section 222 sets a second resonance frequency fr_2 for determination as a frequency which is less than or equal to the first antiresonant frequency fa_1 for determination. Afterward, the Vdc calculation section calculates a second bias voltage value Vdc_2 in accordance with $Vdc\_2 = f^{-1}(fr\_2)$ on the basis of the second resonance frequency fr_2 for determination and the function f. The Vdc calculation section 222 outputs the calculated second bias voltage value Vdc_2 to the fr and fa calculation section 224.

The fr and fa calculation section 224 calculates a second antiresonant frequency fa_2 for determination in accordance with $fa\_2 = g(Vdc\_2)$ on the basis of the second bias voltage value Vdc_2 and the function g. The fr and fa calculation section 224 similarly outputs the calculated second antiresonant frequency fa_2 for determination to the Vdc calculation section 222 as described above.

The Vdc calculation section 222 sets a third resonance frequency fr_3 for determination as a frequency which is less than or equal to the second antiresonant frequency fa_2 for determination. Afterward, the Vdc calculation section similarly calculates a third bias voltage value Vdc_3 in accordance with $Vdc\_3 = f^{-1}(fr\_3)$ on the basis of the third resonance frequency fr_3 for determination and the function f as described above.

The Vdc calculation section 222 and the fr and fa calculation section 224 outputs the first bias voltage value Vdc_1, the second bias voltage value Vdc_2 and the third bias voltage value Vdc_3 to the Vdc determination section 230. The Vdc determination section 230 outputs the input first bias voltage value Vdc_1 to the first bias regulator, outputs the input second bias voltage value Vdc_2 to the second bias regulator, and outputs the input third bias voltage value Vdc_3 to the third bias regulator.

The first bias regulator applies the input first bias voltage value Vdc_1 to the first cMUTs, the second bias regulator outputs the input second bias voltage value Vdc_2 to the second cMUTs, and the third bias regulator outputs the input third bias voltage value Vdc_3 to the third cMUTs.

In consequence, the cMUT array 100 can function in a frequency band of a minimum value of a frequency at which the first cMUTs function to a maximum value of a frequency at which the third cMUTs function. Moreover, the frequency band where the array functions is continuous, and any frequency bands where the array does not function are not present. Consequently, as compared with the first embodiment including the two groups, the whole cMUT array 100 functions in a wider frequency band in the present modification including the three groups.

In the present modification, the first to third bias voltage values are determined in order from the largest bias voltage value. In this case, each bias voltage value can be determined so that the array can securely function in a frequency band on a lower frequency side. That is, such a determining method is advantageous, when information reflected on a side distant from the cMUT array 100 is to be securely acquired.

Additionally, the respective bias voltage values may be determined in order from the smallest bias voltage value. In this case, the method is advantageous, when information reflected on a side close to the cMUT array 100 is to be securely acquired.

It is to be noted that the number of the groups can be four or more similarly to the present modification. When the number of the groups further increases, the frequency band where the array functions can further be expanded. In this case, similarly to the difference between the first embodiment and the modification, the number of the elements may be increased or decreased so that the elements function, in accordance with the number of the groups.

Second Embodiment

A second embodiment of the present invention will be described. Here, the description of the second embodiment is limited to differences from the first embodiment, a common configuration is denoted with the same reference marks, and similar descriptions will be omitted. The first embodiment focuses on acquisition of an image at the position distant from the cMUT array 100. Therefore, in the first embodiment, when the frequency determination section 226 determines that fr_d≤fa_d is false, the frequency resetting section 228 performs resetting to decrease the maximum value frq_up of a frequency band. That is, in the first embodiment for such a case, the ultrasonic probe device sacrifices the image acquisition at a position close to the cMUT array 100.

On the other hand, in the present embodiment, an ultrasonic probe device accurately acquires an image in a range close to an ultrasonic source, and sensitively forms an image of a distant position, i.e., a deep portion. Therefore, in the present embodiment, the bias voltage of the first embodiment is changed with an elapse of time. The whole configuration of the ultrasonic probe device in the present embodiment is about the same as the configuration in the first embodiment described with reference to FIG. 1. However, the present embodiment is different in part of configurations of a control unit 210 and a band control unit 220.

The configuration of the control unit 210 according to the present embodiment is shown in FIG. 6. The control unit 210 according to the present embodiment includes an initial frequency setting section 212, a final frequency setting section 214, and a maximum receiving period calculation section 216.

An input unit 410 which is, for example, a keyboard acquires, from a user, a range of a distance between a cMUT array to a position from which an image is acquired. Here, a distance between the cMUT array 100 and an end of the range which is close to the cMUT array 100 is a depth L1, and a distance between the cMUT array 100 and the other end of the range which is distant from the cMUT array 100 is a depth L2. The input unit 410 outputs values of the acquired depths L1 and L2 to the control unit 210.

The initial frequency setting section 212 determines a maximum value frq_up on the basis of the input depth L1. Here, the initial frequency setting section 212 may determine the maximum value frq_up on the basis of a table indicating a relation between the depth L1 and the maximum value frq_up, or may calculate the maximum value frq_up in accordance with an equation indicating the relation between the depth L1 and the maximum value frq_up.

Similarly, the final frequency setting section 214 determines a minimum value frq_low at which the cMUT array 100 functions, on the basis of the input depth L2. Here, the final frequency setting section 214 may determine the minimum value frq_low on the basis of a table indicating a relation between the depth L2 and the minimum value frq_low, or may calculate the minimum value frq_low in accordance with an equation indicating the relation between the depth L2 and the minimum value frq_low.

Moreover, the maximum receiving period calculation section 216 calculates a maximum receiving period T in accordance with the depth L2 and, for example, the following equation (7):

$$T=2\times L2/c, \quad (7)$$

where c is a sound speed in a medium. Therefore, the maximum receiving period T obtained by the equation (7) is a period of time when an ultrasonic wave travels forwards and backwards between the cMUT array 100 to the most distant position from which the image is to be acquired (the depth L2).

As shown in FIG. 6, the control unit 210 outputs the maximum value frq_up, the minimum value frq_low and the maximum receiving period T to the band control unit 220.

Figure 7:
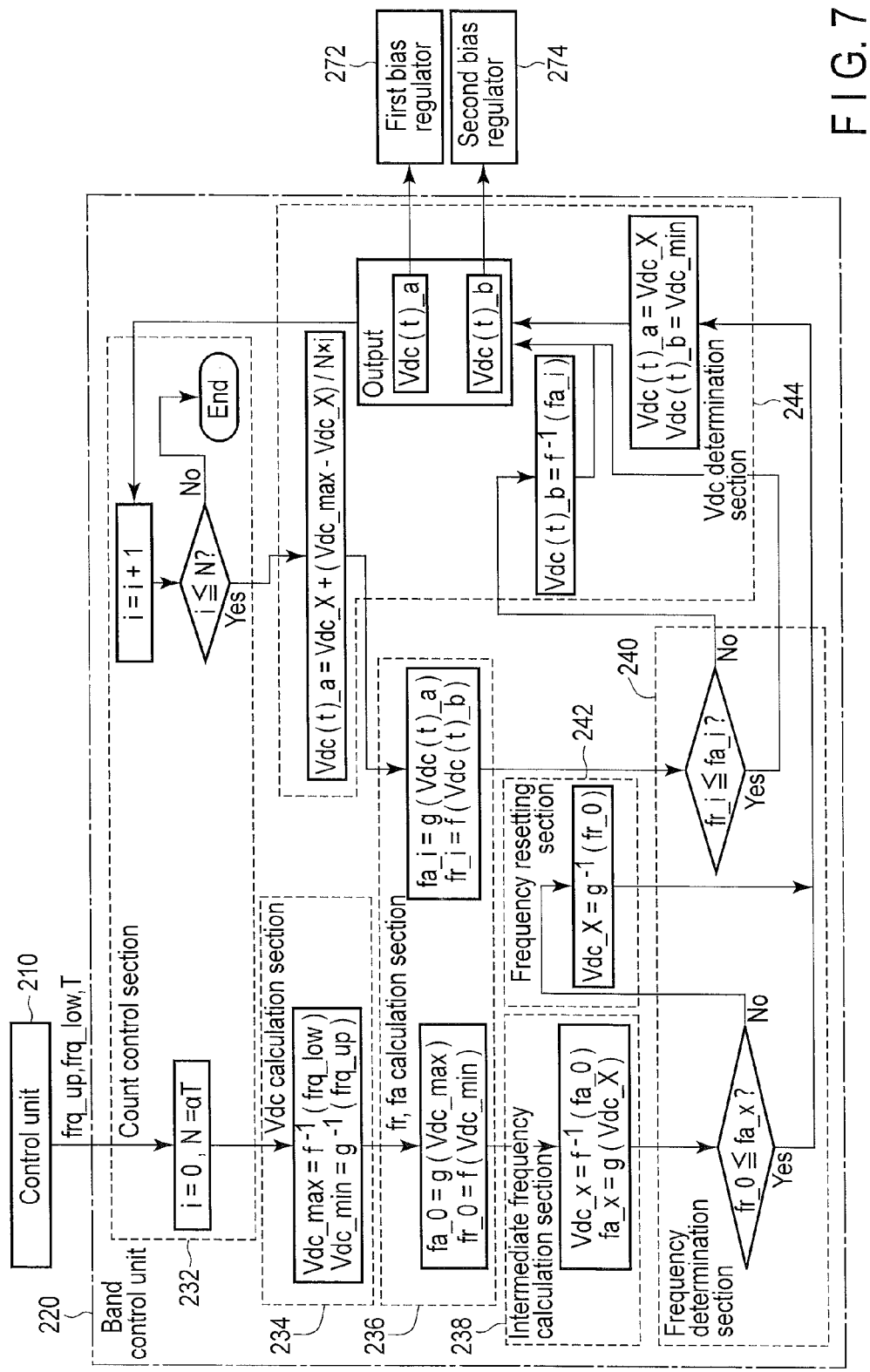
FIG. 7 is a block diagram showing a configuration example of a part concerned with determination of a bias voltage to be applied to each cMUT of the ultrasonic probe device according to the second embodiment of the present invention.

As shown in FIG. 7, the band control unit 220 includes a count control section 232, a Vdc calculation section 234, an fr and fa calculation section 236, an intermediate frequency calculation section 238, a frequency determination section 240, a frequency resetting section 242, and a Vdc determination section 244.

First, the count control section 232 in the band control unit 220 sets a variable i for count to zero. Moreover, the count control section 232 calculates a bias pitch number N in accordance with N=αT on the basis of the maximum receiving period T input from the control unit 210 by use of, for example, a constant α.

Next, the Vdc calculation section 234 calculates a bias voltage maximum value Vdc_max from the minimum value frq_low in accordance with the following equation (8):

$$Vdc\_\max=f^{-1}(\text{frq\_low}). \quad (8)$$

Moreover, the Vdc calculation section 234 calculates a bias voltage minimum value Vdc_min from the maximum value frq_up in accordance with the following equation (9):

$$Vdc\_\min=g^{-1}(\text{frq\_up}). \quad (9)$$

Figure 8:
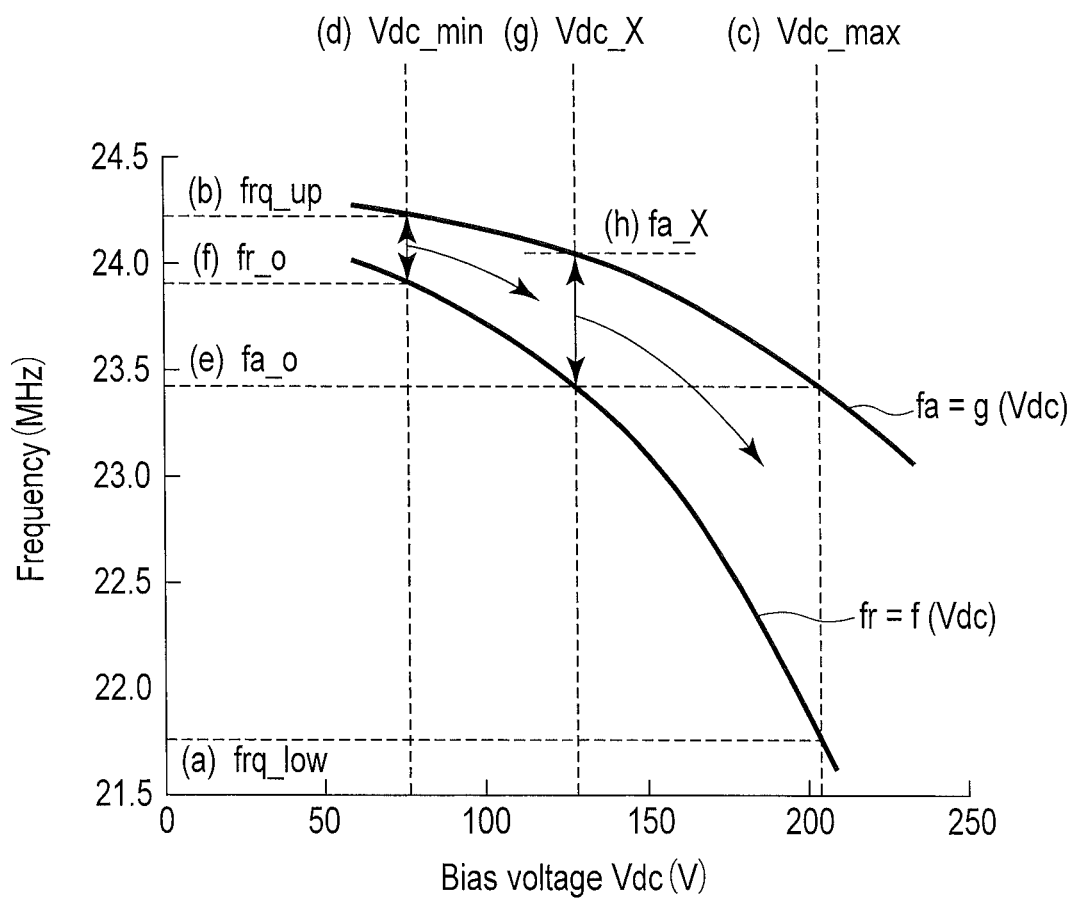
FIG. 8 is a diagram for explaining an example of the bias voltage to be applied to the cMUT of the ultrasonic probe device according to the second embodiment of the present invention.

Hereinafter, each operation will be described with reference to FIG. 8 showing an example. The ultrasonic probe device according to the present embodiment allows the cMUT array 100 to function in the frequency band of frequencies of (a) frq_low to (b) frq_up. Therefore, as described above, first in the present calculation, (c) Vdc_max is obtained from (a) frq_low, and (d) Vdc_min is obtained from (b) frq_up in, for example, FIG. 8.

The fr and fa calculation section 236 calculates an antiresonant frequency value fa_0 for determination at the bias voltage Vdc_max, from the bias voltage maximum value Vdc_max calculated by the Vdc calculation section 234 in accordance with the following equation (10):

$$fa\_0=g(Vdc\_\max). \quad (10)$$

Moreover, the fr and fa calculation section 236 calculates a resonance frequency value fr_0 for determination at the bias voltage Vdc_min, from the bias voltage minimum value Vdc_min calculated by the Vdc calculation section 234 in accordance with the following equation (11):

$$fr\_0=f(Vdc\_\min). \quad (11)$$

By the present calculation, for example, (e) fa_0 and (f) fr_0 in FIG. 8 are obtained. Additionally, in the following description, the resonance frequency for determination and the antiresonant frequency for determination will simply be referred to as the resonance frequency and the antiresonant frequency, respectively.

The intermediate frequency calculation section 238 calculates a bias voltage Vdc_X from the antiresonant frequency fa_0 calculated by the fr and fa calculation section 236, in accordance with the following equation (12):

$$Vdc\_X = f^{-1}(fa\_0). \quad (12)$$

Next, the intermediate frequency calculation section 238 calculates an antiresonant frequency fa_x at the application of the bias voltage Vdc_X, from the calculated bias voltage Vdc_X in accordance with the following equation (13):

$$fa\_X = g(Vdc\_X). \quad (13)$$

By the present calculation, for example, (g) Vdc_X and (h) fa_X in FIG. 8 are obtained.

The frequency determination section 240 determines whether fr_0≤fa_X or not. When fr_0≤fa_x is true, the Vdc determination section 244 sets a first bias voltage Vdc(t)_a to the Vdc_X, and sets a second bias voltage Vdc(t)_b to the Vdc_min. The Vdc determination section 244 outputs the set first bias voltage Vdc(t)_a to a first bias regulator 272, and outputs the set second bias voltage Vdc(t)_b to a second bias regulator 274. In the example shown in FIG. 8, fr_0≤fa_X.

As described above, when i=0, the bias voltage Vdc_X is applied to first cMUTs 130 controlled by the first bias regulator 272 so that the first cMUTs function from the antiresonant frequency fa_0 to the antiresonant frequency fa_X (the frequency fa_0 is the antiresonant frequency at the Vdc_max, but becomes the resonance frequency at the Vdc_X). Moreover, when i=0, the bias voltage minimum value Vdc_min is applied to second cMUTs 140 controlled by the second bias regulator 274 so that the second cMUTs function from the resonance frequency fr_0 to the maximum value frq_up. In consequence, when i=0, the cMUT array 100 including the first cMUTs 130 and the second cMUTs 140 functions from the resonance frequency fa_0 to the maximum value frq_up.

On the other hand, when the frequency determination section 240 determines that fr_0≤fa_X is false, the frequency resetting section 242 resets the Vdc_X in accordance with the following equation (14):

$$Vdc\_X = g^{-1}(fr\_0). \quad (14)$$

In the case of even when the bias voltage as a first candidate is applied in the present processing, the frequency band where the first cMUTs 130 function does not overlap with the frequency band where the second cMUTs 140 function, the Vdc_X is reset to a smaller value so that these two frequency bands overlap with each other.

Afterward, the Vdc determination section 244 sets the first bias voltage Vdc(t)_a to the Vdc_X reset by the frequency resetting section 242, and sets the second bias voltage Vdc(t)_b to the Vdc_min. The Vdc determination section 244 outputs the set first bias voltage Vdc(t)_a to the first bias regulator 272, and outputs the set second bias voltage Vdc(t)_b to the second bias regulator 274.

When the outputs to the first bias regulator 272 and the second bias regulator 274 end, the count control section 232 resets to i=i+1. Next, the count control section 232 determines whether i≤N or not. When the count control section 232 determines that I≤N is false, the output processing to the first bias regulator 272 and the second bias regulator 274 is ended.

On the other hand, when i≤N is true, the Vdc determination section 244 determines the first bias voltage Vdc(t)_a in accordance with the following equation (15):

$$Vdc(t)\_a = Vdc\_X + (Vdc\_\max - Vdc\_X)/N \times i. \quad (15)$$

That is, the bias voltage Vdc(t)_a to be applied to the first cMUTs 130 is increased as much as a voltage obtained by equally dividing a difference between the Vdc_X and the Vdc_max by the bias pitch number N.

The fr and fa calculation section 236 calculates a value of an antiresonant frequency fa_i at the bias voltage Vdc(t)_a, from the first bias voltage Vdc(t)_a in accordance with the following equation (16):

$$fa\_i = g(Vdc(t)\_a). \quad (16)$$

Moreover, the fr and fa calculation section 236 calculates a value of a resonance frequency fr_i at the bias voltage Vdc(t)_b, from the second bias voltage Vdc(t)_b in accordance with the following equation (17):

$$fr\_i = f(Vdc(t)b). \quad (17)$$

The frequency determination section 240 determines whether fr_i≤fa_i or not.

When fr_i≤fa_i is true, the Vdc determination section 244 outputs the first bias voltage Vdc(t)_a to the first bias regulator 272, and outputs the second bias voltage Vdc(t)_b to the second bias regulator 274. That is, in the case of when the increased first bias voltage Vdc(t)_a is applied to the first cMUTs 130 and the second bias voltage Vdc(t)_b which is not changed is applied to the second cMUTs 140, the frequencies at which the first and second cMUTs function overlap with each other, the second bias voltage Vdc(t)_b is not changed from the previous value and is applied to the second cMUTs 140.

On the other hand, when fr_i≤fa_i is false, the Vdc determination section 244 resets the Vdc(t)_b in accordance with the following equation (18):

$$Vdc(t)\_b = f^{-1}(fa\_i). \quad (18)$$

Afterward, the Vdc determination section 244 outputs the Vdc(t)_a as the bias voltage to the first bias regulator 272, and outputs the reset Vdc(t)_b as the bias voltage to the second bias regulator 274. That is, according to the present processing, the second bias voltage Vdc(t)_b so that the frequency band where the first cMUTs 130 function is adjacent to the frequency band where the second cMUTs 140 function.

After the outputs to the first bias regulator 272 and the second bias regulator 274 by the Vdc determination section 244, the count control section 232 sets i=i+1, and again determines whether i≤N or not. Subsequently, while i≤N, the above processing is repeated. Additionally, control is executed by the count control section 232 so that the processing is performed every (1/α) time.

In this way, for example, the Vdc determination section 230 functions as a bias voltage determination section.

Figure 9A:
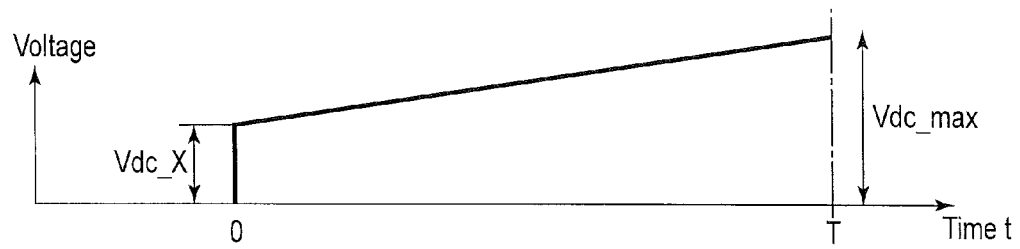
FIG. 9A is a diagram schematically showing a bias voltage to be applied to each first cMUT of the ultrasonic probe device according to the second embodiment of the present invention.
Figure 9B:
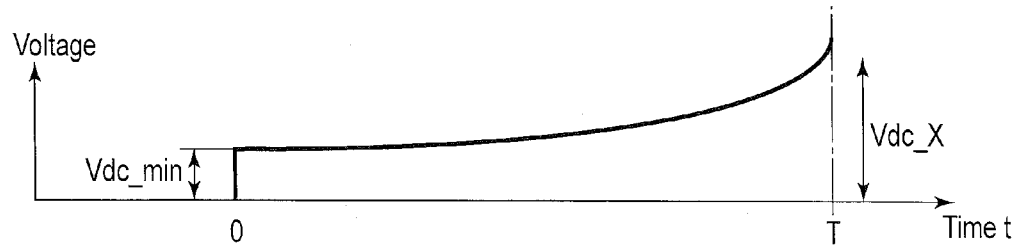
FIG. 9B is a diagram schematically showing a bias voltage to be applied to each second cMUT of the ultrasonic probe device according to the second embodiment of the present invention.

In consequence, as shown in FIG. 9A, the bias voltage to be applied to the first cMUTs 130 increases at a predetermined ratio from the Vdc_X to the Vdc_max with the elapse of time. Moreover, as shown in FIG. 9B, the bias voltage to be applied to the second cMUTs 140 increases from the Vdc_min to the Vdc_X in accordance with the increase of the bias voltage to be applied to the first cMUTs 130 with the elapse of time. As a result, the whole cMUT array 100 including the first cMUTs 130 and the second cMUTs 140 changes from a state where the array functions from the resonance frequency fa_0 to the maximum value frq_up to a state where the array functions from the minimum value frq_low to the antiresonant frequency fa_X with the elapse of time, and the array functions from the minimum value frq_low to the maximum value frq_up through the whole period of time.

Also in the present embodiment, similarly to the first embodiment, when an ultrasonic image is acquired, a pulse generator 260 generates pulses, and the pulses are applied to the first cMUTs 130 and the second cMUTs 140. Here, a timing when the pulses are applied to the first cMUTs 130 and the second cMUTs 140 is a time t=0 (i=0). That is, when pulse waves are emitted, the bias voltage Vdc_X is applied to the first cMUTs 130, and the bias voltage Vdc_min is applied to the second cMUTs 140. Then, after the emission of the pulse waves, the bias voltages applied to the first cMUTs 130 and the second cMUTs 140 increase.

As described above, also in the present embodiment, similarly to the first embodiment, when the ultrasonic image is acquired, the pulse generator 260 generates the pulses under the control of the control unit 210. The generated pulses are applied to the first cMUTs 130 via the first bias regulator 272, and applied to the second cMUTs 140 via the second bias regulator 274.

The first cMUTs 130 emit the pulse waves in a state where the bias voltage value Vdc_X is applied, and then receive the ultrasonic waves reflected in an irradiation object, while increasing the applied bias voltage. Similarly, the second cMUTs 140 emit the pulse waves in a state where the bias voltage value Vdc_min is applied, and then receive the ultrasonic waves reflected in the irradiation object, while increasing the applied bias voltage.

By vibration of an upper electrode 112 of each of the cMUTs 110 which have received the reflected waves, a potential difference between the upper electrode 112 and a lower electrode 114 changes. The potential difference between the upper electrode 112 and the lower electrode 114 in each of the cMUTs 110 is amplified by each of amplifiers 310, and the amplified signal is subjected to A/D conversion by each of A/D converters 320. A beam combining circuit 330 acquires an image signal on the basis of a digital echo signal obtained by the conversion. This image signal is transmitted to a display unit 420 via a DSC 340, and the display unit 420 displays an image on the basis of this image signal.

As described above, with the elapse of time, the bias voltage to be applied to the first cMUTs 130 increases from the Vdc_X to the Vdc_max, and the bias voltage to be applied to the second cMUTs 140 increases from the Vdc_min to the Vdc_X. As a result, the frequency band where the cMUT array 100 including the first cMUTs 130 and the second cMUTs 140 functions is comparatively high immediately after the emission of the pulse wave, and then the frequency band where the array functions gradually becomes low.

The ultrasonic waves received by the cMUT array 100 immediately after the emission of the pulse waves are ultrasonic waves reflected in the vicinity of the cMUT array 100, and hence the ultrasonic waves include a large amount of comparatively high frequency components. Afterward, with the elapse of time, the ultrasonic waves received by the cMUT array 100 are reflected at a position gradually distant from the cMUT array 100, and hence the ultrasonic waves include a large amount of gradually low frequency components.

That is, according to the present embodiment, the frequency band where the cMUT array 100 functions changes at an appropriate timing in accordance with the frequency components included in the received ultrasonic waves which change with the elapse of time. As a result, the cMUT array 100 can efficiently receive the ultrasonic waves, have a suitable receiving sensitivity, and improve a quality of the acquired image. Further in the present embodiment, effects similar to those of the first embodiment can be obtained.

Additionally, in the present embodiment, when a region close to the cMUT array 100 is formed into an image, both the frq_up and the frq_low increase, and hence all the Vdc_min, the Vdc_X and the Vdc_max decrease. The Vdc(t)_a and the Vdc(t)_b also shift at small values.

It is to be noted that in the above description, the bias voltage is increased from the time t=0, but the embodiment may have, for example, a configuration where after the emission of the pulse wave, a standby time is set as much as a time when the ultrasonic wave travels forwards and backwards between the cMUT array 100 and the position closest to the array from which the image is to be acquired, i.e., t1=2×L1/c (where c is a sound speed in a medium), and after the standby time, the bias voltage is increased. In this case, the time when the bias voltage is increased is t1 shorter than the maximum receiving period T. Thus, the bias pitch number N decreases to, for example, N=α(T−t1).

Modification of Second Embodiment

A modification of the second embodiment which is limited to differences from the second embodiment will be described. In the second embodiment, the cMUTs 110 of the cMUT array 100 are divided into two groups of the first cMUTs 130 and the second cMUTs 140. In the present modification, the cMUTs 110 of the cMUT array 100 are divided into three groups.

Therefore, the cMUT array 100 includes the first cMUTs, the second cMUTs and the third cMUTs. Moreover, a bias voltage of the first cMUTs is regulated by a first bias regulator, a bias voltage of the second cMUTs is regulated by a second bias regulator, and a bias voltage of the third cMUTs is regulated by a third bias regulator.

Also in this case, as shown in FIG. 10, a Vdc calculation section 234 calculates bias voltages Vdc_min and Vdc_max so that the cMUT array 100 functions in a frequency band of a minimum value frq_low to a maximum value frq_up. Afterward, similarly to the second embodiment, an fr and fa calculation section 236, an intermediate frequency calculation section 238, a frequency determination section 240 and a frequency resetting section 242 calculate Vdc_a(0), Vdc_b(0) and Vdc_c(0) which are bias voltage values at t=0, concerning voltages to be applied to the cMUTs 110 of the three groups, respectively, i.e., a first bias voltage Vdc_a(t), a second bias voltage Vdc_b(t) and a third bias voltage Vdc_c(t), as shown in FIG. 10.

For example, the Vdc calculation section 234 calculates the maximum bias voltage value Vdc_max in accordance with Vdc_max=$f^{-1}$(frq_low) on the basis of the input frequency band minimum value frq_low and a function f. The Vdc calculation section 234 outputs the calculated maximum bias voltage value Vdc_max to the fr and fa calculation section 236.

The fr and fa calculation section 236 calculates a first antiresonant frequency fa_1 for determination in accordance with fa_1=g(Vdc_max) on the basis of the input maximum bias voltage value Vdc_max and a function g. Differently from the second embodiment, in the present modification, the fr and fa calculation section 236 outputs the calculated first antiresonant frequency fa_1 for determination to the Vdc calculation section 234.

Next, the Vdc calculation section 234 sets a first resonance frequency fr_1 for determination as a frequency which is less than or equal to the first antiresonant frequency fa_1 for determination. Afterward, the Vdc calculation section 234 calculates the first bias voltage value Vdc_a(0) in accordance with Vdc_a(0)=f$^{-1}$(fr_1) on the basis of the first resonance frequency fr_1 for determination and the function f. The Vdc calculation section 234 outputs the calculated first bias voltage value Vdc_a(0) to the fr and fa calculation section 236.

The fr and fa calculation section 236 calculates a second antiresonant frequency fa_2 for determination in accordance with fa_2=g(Vdc_a(0)) on the basis of the input first bias voltage value Vdc_a(0) and the function g. As described above, the fr and fa calculation section 236 similarly outputs the calculated second antiresonant frequency fa_2 for determination to the Vdc calculation section 234.

Next, the Vdc calculation section 234 sets a second resonance frequency fr_2 for determination as a frequency which is less than or equal to the second antiresonant frequency fa_2 for determination. Afterward, the Vdc calculation section 234 calculates the second bias voltage value Vdc_b(0) in accordance with Vdc_b(0)=f$^{-1}$(fr_2) on the basis of the second resonance frequency fr_2 for determination and the function f. The Vdc calculation section 234 outputs the calculated second bias voltage value Vdc_b(0) to the fr and fa calculation section 236.

The fr and fa calculation section 236 calculates a third antiresonant frequency fa_3 for determination in accordance with fa_3=g(Vdc_b(0)) on the basis of the input second bias voltage Vdc_b(0) and the function g. As described above, the fr and fa calculation section 236 similarly outputs the calculated third antiresonant frequency fa_3 for determination to the Vdc calculation section 234.

Next, the Vdc calculation section 234 sets a third resonance frequency fr_3 for determination as a frequency which is less than or equal to the third antiresonant frequency fa_3 for determination. Afterward, the Vdc calculation section 234 calculates the third bias voltage value Vdc_c(0) in accordance with Vdc_b(0)=f$^{-1}$(fr_3) on the basis of the third resonance frequency fr_3 for determination and the function f. The Vdc calculation section 234 outputs the calculated third bias voltage value Vdc_c(0) to the fr and fa calculation section 236.

The fr and fa calculation section 236 calculates a fourth antiresonant frequency fa_4 for determination in accordance with fa_4=g(Vdc_(0)) on the basis of the input third bias voltage value Vdc_c(0) and the function g.

The frequency determination section 240 determines whether the fourth antiresonant frequency fa_4 for determination is more than or equal to the maximum value frq_up. When the fourth antiresonant frequency fa_4 for determination is less than the maximum value frq_up, the first bias voltage value Vdc_a(0), the second bias voltage value Vdc_b(0) and the third bias voltage value Vdc_c(0) are reset to small values.

When the frequency determination section 240 determines that the fourth antiresonant frequency fa_4 for determination is more than or equal to the maximum value frq_up, a Vdc determination section 244 outputs the first bias voltage value Vdc_a(0) to the first bias regulator, outputs the second bias voltage value Vdc_b(0) to the second bias regulator, and outputs the third bias voltage value Vdc_c(0) to the third bias regulator, respectively.

Afterward, the Vdc determination section 244 gradually increases the first bias voltage value Vdc_a(t) from the Vdc_a(0) to the Vdc_max at t=T with an elapse of time. Moreover, the Vdc determination section 244 determines the Vdc_b(t) as, for example, $$g(Vdc\_a(t))=f(Vdc\_b(t)). \quad (19)$$

The Vdc determination section 244 determines the Vdc_c (t) as, for example, $$g(Vdc\_b(t))=f(Vdc\_c(t)). \quad (20)$$

In this way, the bias voltages are regulated so that frequency bands of ultrasonic waves emitted by the first cMUTs, the second cMUTs and the third cMUTs are continuous. Another setting method may be used, as long as the bias voltages are set so that the frequency bands are continuous.

The Vdc determination section 244 outputs the first bias voltage Vdc_a(t) to the first bias regulator, outputs the second bias voltage Vdc_b(t) to the second bias regulator, and outputs the third bias voltage Vdc_c(t) to the third bias regulator. The first bias regulator applies the bias voltage to the first cMUTs, the second bias regulator applies the bias voltage to the second cMUTs, and the third bias regulator applies the bias voltage to the third cMUTs.

As described above, according to the present modification, the number of the groups of the cMUTs 110 of the cMUT array 100 can be increased. When the number of the groups is further increased, the whole cMUT array 100 can function in a wider frequency band. Furthermore, advantages similar to those of the second embodiment can be obtained.

Additionally, the example shown in FIG. 10 is a special example where g(Vdc_max)=f(Vdc_a(0)), g(Vdc_a(0))=f(Vdc_b(0)), g(Vdc_b(0))=f(Vdc_c(0)), and g(Vdc_c(0))=f(Vdc_min).

Moreover, in the above method of determining the bias voltage values, the frequency determination section 240 determines whether the fourth antiresonant frequency fa_4 for determination is more than or equal to the maximum value frq_up, but when the cMUT array 100 does not have to function up to the maximum value frq_up of the frequency band, this determination is not necessary. In this case, the Vdc determination section 244 determines the bias voltage values in order from the largest bias voltage value, and hence the respective bias voltage values can be determined so that the array can securely function in the frequency band on a low frequency side. That is, such a determining method is advantageous, when information reflected on a side distant from the cMUT array 100 is to be securely acquired.

Furthermore, the Vdc determination section 244 may determine the respective bias voltage values in order from the smallest bias voltage value. In this case, the determining method is advantageous, when information reflected on a side close to the cMUT array 100 is to be securely acquired.

Additionally, the number of the groups can be four or more similarly to the present modification. When the number of the groups further increases, the frequency band where the array functions can further be expanded. In this case, similarly to the difference between the second embodiment and the present modification, the number of the elements can be increased or decreased in accordance with the number of the groups.

Third Embodiment

A third embodiment of the present invention will be described. Here, the description of the third embodiment is limited to differences from the second embodiment, a common configuration is denoted with the same reference marks, and similar descriptions will be omitted. In the second embodiment, the first bias voltage Vdc_a(t) and the second bias voltage Vdc_b(t) are simultaneously changed. On the other hand, the present embodiment is suitable for a case where, for example, a portion close to a cMUT array 100 is especially accurately formed into an image, and the like.

In first cMUTs 130 and second cMUTs 140, a bias voltage to be applied to the second cMUTs 140 to which a comparatively low bias voltage is applied and which function in a comparatively high frequency band is not changed for a while after a pulse wave is emitted. Afterward, with an elapse of time when all ultrasonic waves reflected in the vicinity of the cMUT array 100 are considered to reach the cMUT array 100, the bias voltage to be applied to the second cMUTs 140 is increased. On the other hand, a bias voltage to be applied to the first cMUTs 130 to which a comparatively high bias voltage is applied and which function in a comparatively low frequency band is increased immediately after the pulse wave is emitted, until the bias voltage to be applied to the second cMUTs 140 starts to be increased. Afterward, when the bias voltage to be applied to the second cMUTs 140 starts to be increased, the bias voltage to be applied to the first cMUTs 130 is maintained at a predetermined value.

Figure 11:
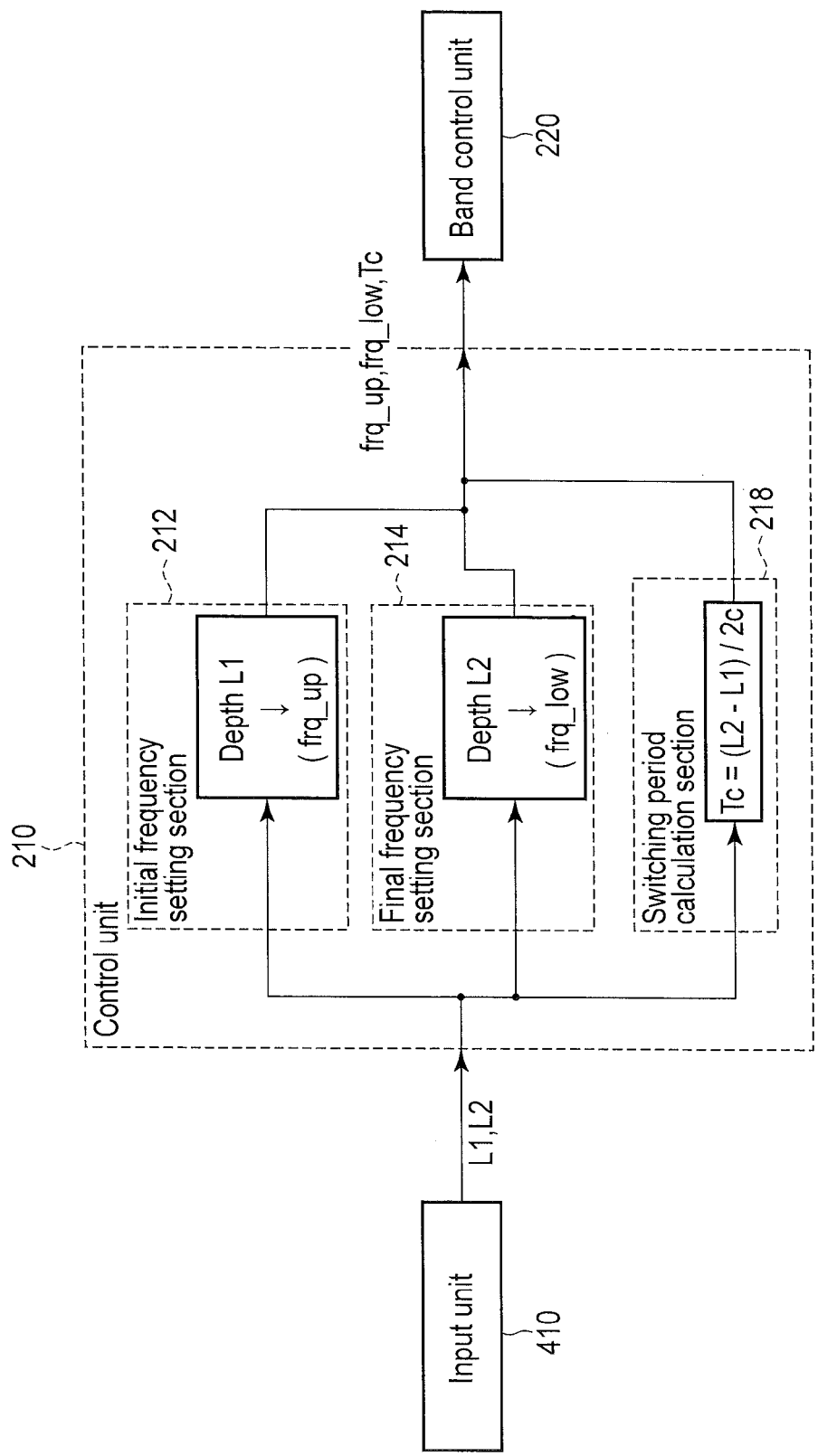
FIG. 11 is a block diagram showing a configuration example of a part concerned with determination of a bias voltage to be applied to each cMUT of the ultrasonic probe device according to a third embodiment of the present invention.

A configuration of a control unit 210 according to the present embodiment is shown in FIG. 11. In the control unit 210 according to the present embodiment, the maximum receiving period calculation section 216 of the control unit 210 according to the second embodiment described with reference to FIG. 6 is replaced with a switching period calculation section 218. The switching period calculation section 218 calculates a switching period Tc by use of depths L1 and L2 in accordance with, for example, the following equation (21):

$$T = (L2 - L1)/2c, \quad (21)$$

where c is a sound speed of a medium. Therefore, the switching period Tc obtained by the equation (21) indicates a time when the ultrasonic wave travels forwards and backwards from the cMUT array 100 to an intermediate position between a position closest to the array and a position most distant from the array from which an image is to be acquired.

As shown in FIG. 11, the control unit 210 outputs a maximum value frq_up, a minimum value frq_low and the switching period Tc to a band control unit 220.

Figure 12:
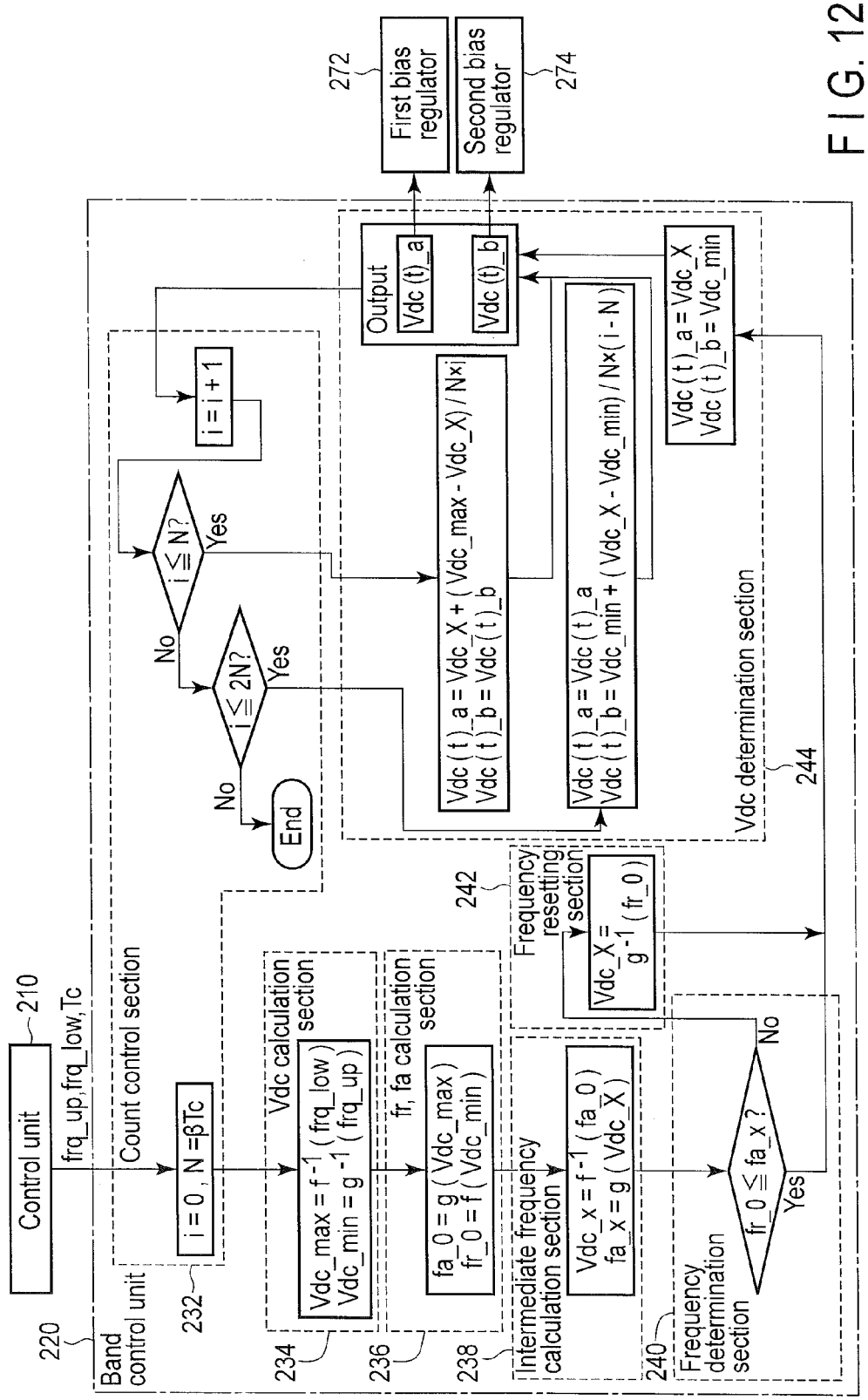
FIG. 12 is a block diagram showing a configuration example of a part concerned with determination of a bias voltage to be applied to each cMUT of the ultrasonic probe device according to a third embodiment of the present invention.

A difference in operation of the band control unit 220 between the second embodiment and the present embodiment will be described with reference to FIG. 12. First, a count control section 232 in the band control unit 220 sets a variable i for count to zero. Moreover, the count control section 232 calculates a bias pitch number N in accordance with $N = \beta Tc$ on the basis of the switching period Tc input from the control unit 210 by use of, for example, a constant $\beta$.

Afterward, similarly to the second embodiment, a Vdc calculation section 234, an fr and fa calculation section 236, an intermediate frequency calculation section 238, a frequency determination section 240 and a frequency resetting section 242 calculate Vdc_X which is an initial value of a first bias voltage value Vdc(t)_a, and Vdc_min which is an initial value of a second bias voltage value Vdc(t)_b.

Afterward, a Vdc determination section 244 sets the first bias voltage Vdc(t)_a to the Vdc_X, and sets the second bias voltage Vdc(t)_b to the Vdc_min. The Vdc determination section 244 outputs the set first bias voltage Vdc(t)_a to a first bias regulator 272, and outputs the set second bias voltage Vdc(t)_b to a second bias regulator 274.

After the outputs to the first bias regulator 272 and the second bias regulator 274 by the Vdc determination section 244, the count control section 232 resets i=i+1. Next, the count control section 232 determines whether i≤N or not. When i≤N is true, the Vdc determination section 244 determines the first bias voltage Vdc(t)_a in accordance with the following equation (22):

$$Vdc(t)\_a = Vdc\_X + (Vdc\_\max - Vdc\_X)/N \times i, \quad (22)$$

and determines the second bias voltage Vdc(t)_b in accordance with the following equation (23):

$$Vdc(t)\_b = Vdc(t)\_b. \quad (23)$$

That is, the Vdc determination section 244 increases the bias voltage Vdc(t)_a to be applied to the first cMUTs 130 as much as a voltage obtained by equally dividing a difference between the Vdc_X and the Vdc_max by the bias pitch number N. On the other hand, the Vdc determination section 244 does not change the bias voltage Vdc(t)_b to be applied to the second cMUTs 140.

Afterward, the Vdc determination section 244 outputs the Vdc(t)_a as the bias voltage to the first bias regulator 272, and outputs the Vdc(t)_b as the bias voltage to the second bias regulator 274.

After the outputs to the first bias regulator 272 and the second bias regulator 274 by the Vdc determination section 244, the count control section 232 sets i=i+1, and again determines whether i≤N or not. Subsequently, while i≤N is true, the above processing is repeated. Additionally, control is executed by the count control section 232 so that the processing is performed every $(1/2\beta)$ time.

On the other hand, when i≤N is false, the count control section 232 determines whether i≤2N or not. When i≤2N is true, the Vdc determination section 244 determines the first bias voltage Vdc(t)_a in accordance with the following equation (24):

$$Vdc(t)\_a = Vdc(t)\_a, \quad (24)$$

and determines the second bias voltage Vdc(t)_b in accordance with the following equation (25):

$$Vdc(t)\_b = Vdc\_\min + (Vdc\_X - Vdc\_\min)/N \times (i - N) \quad (25)$$

That is, the Vdc determination section 244 does not change the bias voltage Vdc(t)_a to be applied to the first cMUTs 130. On the other hand, the Vdc determination section 244 increases the bias voltage Vdc(t)_b to be applied to the second cMUTs 140, as much as a voltage obtained by equally dividing a difference between the Vdc_min and the Vdc_X by the bias pitch number N.

Afterward, the Vdc determination section 244 outputs the Vdc(t)_a as the bias voltage to the first bias regulator 272, and outputs the Vdc(t)_b as the bias voltage to the second bias regulator 274.

After the outputs to the first bias regulator 272 and the second bias regulator 274 by the Vdc determination section 244, the count control section 232 sets i=i+1, and again determines whether i≤N or not and whether i≤2N or not. Subsequently, while I≤2N, the above processing is repeated. Additionally, control is executed by the count control section 232 so that the processing is performed every $(1/2\beta)$ time. Afterward, when i≤2N is not true any more, the output processing to the first bias regulator 272 and the second bias regulator 274 is ended.

Figure 13A:
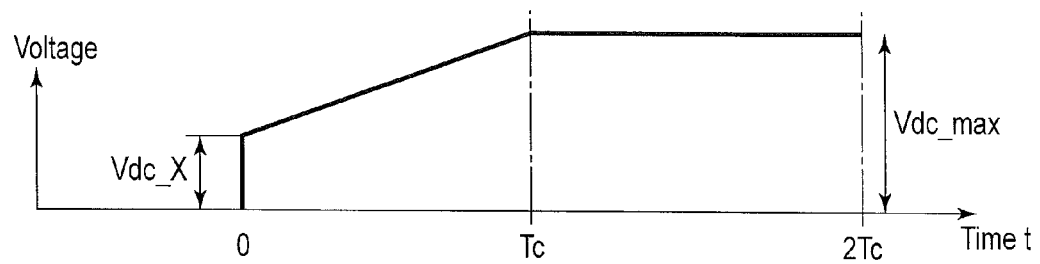
FIG. 13A is a diagram schematically showing a bias voltage to be applied to each first cMUT of the ultrasonic probe device according to the third embodiment of the present invention.

In consequence, as shown in FIG. 13A, the bias voltage to be applied to the first cMUTs 130 increases at a predetermined ratio from the Vdc_X to the Vdc_max with the elapse of time from time t=0 to t=Tc. That is, as shown in FIG. 8, the first cMUTs 130 change from a state where the cMUTs function from the resonance frequency fa_0 to the antiresonant frequency fa_X to a state where the cMUTs function from the minimum value frq_low to the antiresonant frequency fa_0 with the elapse of time. Afterward, the bias voltage to be applied to the first cMUTs 130 becomes constant at the Vdc_max for a period of time t=Tc to t=2Tc. That is, the first cMUTs 130 are maintained in the state where the cMUTs function from the minimum value frq_low to the fa_0.

Figure 13B:
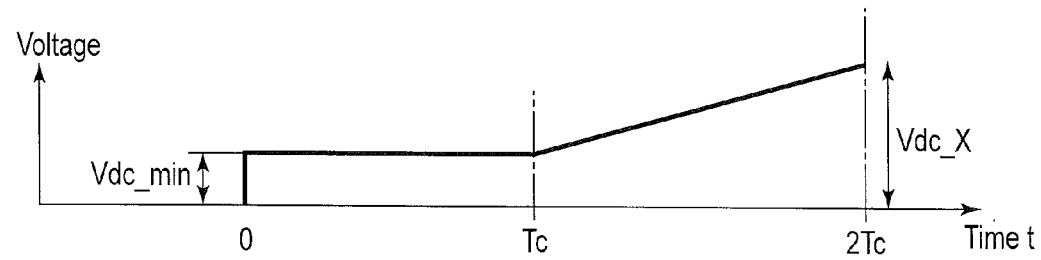
FIG. 13B is a diagram schematically showing a bias voltage to be applied to each second cMUT of the ultrasonic probe device according to the third embodiment of the present invention.

Moreover, as shown in FIG. 13B, the bias voltage to be applied to the second cMUTs 140 becomes constant at the Vdc_min for a period of time t=0 to t=Tc. That is, as shown in FIG. 8, the second cMUTs 140 are maintained in a state where the cMUTs function from the resonance frequency fr_0 to the maximum value frq_up. Afterward, the bias voltage to be applied to the second cMUTs 140 increases at a predetermined ratio from the Vdc_min to the Vdc_X with the elapse of time for the period of time t=Tc to t=2Tc. That is, with the elapse of time, the second cMUTs 140 changes from the state where the cMUTs function from the resonance frequency fr_0 to the maximum value frq_up to the state where the cMUTs function from the resonance frequency fa_0 to the antiresonant frequency fa_X.

Also in the present embodiment, similarly to the second embodiment, when an ultrasonic image is acquired, the pulse generator 260 generates pulses, and the pulses are applied to the first cMUTs 130 and the second cMUTs 140. Here, a timing when the pulses are applied to the first cMUTs 130 and the second cMUTs 140 is the time t=0 (i=0). That is, when pulse waves are emitted, the bias voltage Vdc_X is applied to the first cMUTs 130, and the bias voltage Vdc_min is applied to the second cMUTs 140. Then, after the emission of the pulse waves, the bias voltage to be applied to the first cMUTs 130 increases until the time t=Tc, and then becomes constant, and the bias voltage to be applied to the second cMUTs 140 is constant until the time t=Tc, and then increases.

The first cMUTs 130 emit the pulse waves in a state where the bias voltage value Vdc_X is applied, and then receive the ultrasonic waves reflected in an irradiation object. Similarly, the second cMUTs 140 emit the pulse waves in a state where the bias voltage value Vdc_min is applied, and then receive the ultrasonic waves reflected in the irradiation object. On the basis of signals received by the first cMUTs 130 and the second cMUTs 140, the ultrasonic image is obtained.

According to the present embodiment, the ultrasonic probe device can especially accurately obtain an image from a position close to the cMUT array 100. That is, the ultrasonic waves which are reflected at the position close to the cMUT array 100 to reach the cMUT array 100 have a comparatively high frequency. In the present embodiment, the bias voltage to be applied to the second cMUTs 140 is not changed from the low value Vdc_min until the time Tc after the emission of the pulse waves. That is, the second cMUTs 140 function in a comparatively high frequency band until the time Tc after the emission of the ultrasonic waves. For this period of time, the ultrasonic waves having a comparatively low frequency are received by the first cMUTs in which the bias voltage gradually rises.

After the elapse of the time Tc, the ultrasonic waves which have reached the cMUT array 100 include a large amount of the ultrasonic waves reflected at a position distant from the cMUT array 100, and hence the ultrasonic waves include a large amount of the ultrasonic waves having a comparatively low frequency. Therefore, the frequency band where the second cMUTs 140 function gradually becomes low, and hence the bias voltage to be applied to the second cMUTs 140 gradually becomes high.

In consequence, according to the present embodiment, the ultrasonic probe device can especially accurately obtain the image at the position close to the cMUT array 100, and can suitably receive the ultrasonic waves of the low frequency by the regulation of the bias voltage. Therefore, it is also possible to obtain the suitable image at the position distant from the cMUT array 100.

Moreover, even when the bias voltage to be applied to the second cMUTs is not changed and is kept constant, a similar effect can be obtained.

It is to be noted that the present embodiment has a configuration where the bias voltage to be applied to the second cMUTs 140 is maintained to be low so that the ultrasonic wave of the high frequency is efficiently caught to especially accurately obtain the image at the position close to the cMUT array 100. Conversely, the present embodiment may have a configuration where, for example, the bias voltage to be applied to the first cMUTs 130 is maintained to be high so that the ultrasonic wave of the low frequency is efficiently caught to especially accurately obtain the image at the position distant from the cMUT array 100.

Moreover, when the bias voltage to be applied to the first cMUTs 130 is maintained to be high, the bias voltage to be applied to the second cMUTs 140 may gradually be changed from a high voltage to a low voltage. When the bias voltage is gradually lowered in this way, a sensitivity to the high frequency gradually improves. In consequence, it is possible to obtain the effect that an ultrasonic wave having a higher harmonic component which is generated by nonlinear formation of travel of a sound can be received.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic probe device comprising:
  a plurality of ultrasonic transducers, wherein each of the plurality of ultrasonic transducers is configured to transmit and/or receive ultrasonic waves in a frequency range that varies with a bias voltage value of a bias voltage applied to the each of the plurality of ultrasonic transducers; and
  a band control unit configured to perform a determination function to determine the bias voltage value of the bias voltage applied to the each of the plurality of ultrasonic transducers during an operation period of the plurality of ultrasonic transducers such that a predetermined continuous frequency band is covered by a combination of the frequency ranges of the transmitted and/or received ultrasonic waves from the plurality of ultrasonic transducers,
  wherein the determination function comprises determining:
    a first bias voltage value of a first bias voltage to be applied to a first ultrasonic transducer of the plurality of ultrasonic transducers such that the first ultrasonic transducer transmits and/or receives ultrasonic waves in a first frequency range, and
    a second bias voltage value of a second bias voltage to be applied to a second ultrasonic transducer of the plurality of ultrasonic transducers such that the second ultrasonic transducer transmits and/or receives ultrasonic waves in a second frequency range, at least a part of the second frequency range being different from the first frequency range.

2. The ultrasonic probe device according to claim 1, wherein the band control unit does not change the bias voltage value of the bias voltage applied to the each of the plurality of ultrasonic transducers during the operation period such that the predetermined continuous frequency band is covered by the combination of the frequency ranges of the transmitted and/or received ultrasonic waves from the plurality of ultrasonic transducers.

3. The ultrasonic probe device according to claim 1, further comprising:
a storage unit configured to store bias voltage-frequency relation information indicating a relation between a bias voltage value of a bias voltage to be applied to an ultrasonic transducer of the plurality of ultrasonic transducers and a frequency range of ultrasonic waves transmittable and/or receivable by the ultrasonic transducer of the plurality of ultrasonic transducers at application of the bias voltage,
wherein the band control unit is configured to determine the first bias voltage value and the second bias voltage value based on the bias voltage-frequency relation information stored in the storage unit.

4. The ultrasonic probe device according to claim 3,
wherein the number of the plurality of ultrasonic transducers is m (m is a natural number of 2 or more),
wherein the band control unit is configured to
determine, based on the bias voltage-frequency relation information, the first bias voltage value so that a minimum value of the continuous frequency band is a minimum value of the first frequency band, and
determine, based on the bias voltage-frequency relation information, an n-th bias voltage value (n is a natural number of m or less), when n is 2 or more, so that a minimum value of an n-th frequency range at application of the bias voltage having the n-th bias voltage value to an n-th ultrasonic transducer of the plurality of ultrasonic transducers is less than or equal to a maximum value of the frequency range at application of the bias voltage having an (n−1)-th bias voltage value to an (n−1)-th ultrasonic transducer of the plurality of ultrasonic transducers.

5. The ultrasonic probe device according to claim 4, wherein the band control unit is configured to determine the n-th bias voltage value in ascending order of n.

6. The ultrasonic probe device according to claim 3,
wherein the number of the plurality of ultrasonic transducers is two,
wherein the band control unit is comprised of:
a bias voltage calculation section configured to perform a bias voltage calculation, based on the bias voltage-frequency relation information, the bias voltage calculation comprising calculating:
the first bias voltage value so that a minimum value of the continuous frequency band is a minimum value of the first frequency range, and
the second bias voltage value so that a maximum value of the continuous frequency band is a maximum value of the second frequency range;
a frequency calculation section configured to perform a frequency calculation, based on the bias voltage-frequency relation information, the frequency calculation comprising calculating:
a maximum frequency for determination which is a maximum value of the first frequency range at application of the bias voltage having the first bias voltage value, and
a minimum frequency for determination which is a minimum value of the second frequency range at application of the bias voltage having the second bias voltage value;
a frequency determination section configured to perform a frequency determination comprising determining whether or not the maximum frequency for determination is greater than or equal to the minimum frequency for determination; and
a frequency resetting section configured to reset the maximum value of the continuous frequency band to a smaller value, and cause the bias voltage calculation section to repeat the bias voltage calculation, the frequency calculation section to repeat the frequency calculation and the frequency determination section to repeat the frequency determination, when the maximum frequency for determination is not more than or equal to the minimum frequency for determination.

7. The ultrasonic probe device according to claim 3, wherein the bias voltage-frequency relation information includes
information indicating a relation between the bias voltage value and a minimum value of the frequency range of the ultrasonic waves transmittable and/or receivable by the ultrasonic transducer of the plurality of ultrasonic transducers at application of the bias voltage, wherein the minimum value of the frequency range is a resonance frequency of the ultrasonic transducer, and
information indicating a relation between the bias voltage value and a maximum value of the frequency range of the ultrasonic waves transmittable and/or receivable by the ultrasonic transducer of the plurality of ultrasonic transducers at application of the bias voltage, wherein the maximum value of the frequency range is an antiresonant frequency of the ultrasonic transducer.

8. The ultrasonic probe device according to claim 1, further comprising:
a distance-frequency relation storage unit configured to store information indicating a plurality of relations between a plurality of reaching distances, each of the plurality of reaching distances being a distance from the plurality of ultrasonic transducers to a position in a subject to be reached by the ultrasonic wave, and a minimum value of a frequency of the ultrasonic wave corresponding to the each of the plurality of reaching distances, and
a control unit configured to determine a minimum value of the predetermined continuous frequency band from the reaching distance designated by a user, based on the plurality of relations stored in the distance-frequency relation storage unit.

9. The ultrasonic probe device according to claim 1, wherein the predetermined continuous frequency band varies with time during the operation period.

10. The ultrasonic probe device according to claim 9, wherein the band control unit is configured to determine the bias voltage value of the bias voltage applied to the each of the plurality of ultrasonic transducers during the operation period so that:
a momentary maximum frequency which is a maximum value of the predetermined continuous frequency band monotonously decreases with an elapse of time from a maximum value, and
a momentary minimum frequency which is a minimum value of the predetermined continuous frequency band monotonously decreases with the elapse of time from an initial value to reach a minimum value.

11. The ultrasonic probe device according to claim 10, further comprising:
a storage unit configured to store bias voltage-frequency relation information indicating a relation between a bias voltage value of a bias voltage to be applied to an ultrasonic transducer of the plurality of ultrasonic transducers and a frequency range of ultrasonic waves transmittable and/or receivable by the ultrasonic transducer of the plurality of ultrasonic transducers at application of the bias voltage, wherein the band control unit is configured to determine the bias voltage value of the bias voltage applied to the each of the plurality of ultrasonic transducers during the operation period and a timing to apply the bias voltage based on the bias voltage-frequency relation information stored in the storage unit.

12. The ultrasonic probe device according to claim 11, wherein the number of the plurality of ultrasonic transducers is m (m is a natural number of 2 or more), wherein the band control unit is configured to determine, based on the bias voltage-frequency relation information, the first bias voltage value so that a minimum value of the continuous frequency band is a minimum value of the first frequency range, determine, based on the bias voltage-frequency relation information, the second bias voltage value so that a minimum value of the second frequency range at application of the bias voltage having the second bias voltage value is less than or equal to a maximum value of the first frequency range at application of the bias voltage having the first bias voltage value, change a first applied bias voltage value from the second bias voltage value to the first bias voltage value, with the elapse of time during the operation period, the first applied bias voltage value being a value of an n-th applied bias voltage value (n is a natural number of m or less) when n is 1, the n-th applied bias voltage value being the bias voltage value of the bias voltage to be applied to the n-th ultrasonic transducer of the plurality of ultrasonic transducers, and determine, based on the bias voltage-frequency relation information, the n-th applied bias voltage value so that a minimum value of an n-th frequency range at the application of the bias voltage having the n-th applied bias voltage value to the n-th ultrasonic transducer of the plurality of ultrasonic transducers is less than or equal to a maximum value of the frequency range at application of the bias voltage having an (n−1)-th bias voltage value to an (n−1)-th ultrasonic transducer of the plurality of ultrasonic transducers.

13. The ultrasonic probe device according to claim 12, wherein the band control unit is configured to determine the n-th bias voltage value in ascending order of n.

14. The ultrasonic probe device according to claim 11, wherein the bias voltage-frequency relation information includes information indicating a relation between the bias voltage value and a minimum value of the frequency range of the ultrasonic waves transmittable and/or receivable by the ultrasonic transducer of the plurality of ultrasonic transducers at application of the bias voltage, wherein the minimum value of the frequency range is a resonance frequency of the ultrasonic transducer, and information indicating a relation between the bias voltage value and a maximum value of the frequency range of the ultrasonic waves transmittable and/or receivable by the ultrasound transducer of the plurality of ultrasonic transducers at application of the bias voltage, wherein the maximum value of the frequency range is an antiresonant frequency of the ultrasonic transducer.

15. The ultrasonic probe device according to claim 9, further comprising:

a distance-frequency relation storage unit configured to store information indicating a plurality of relations between a plurality of reaching distances, each of the plurality of reaching distances being a distance from the plurality of ultrasonic transducers to a position in a subject to be reached by the ultrasonic wave, and a minimum value of a frequency of the ultrasonic wave corresponding to the each of the plurality of reaching distances, and a control unit configured to determine a minimum value of the predetermined continuous frequency band from the reaching distance designated by a user, based on the plurality of relations stored in the distance-frequency relation storage unit.

16. A control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of m (m is a natural number of 2 or more) groups, each of the m groups including at least one of the capacitive micromachined ultrasonic transducers, the method comprising:

calculating a first bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage, when n (n is a natural number of m or less) is 1;

determining an n-th bias voltage value so that the minimum value of the transmittable/receivable frequency at the application of the direct-current bias voltage having the n-th bias voltage value is less than or equal to a maximum value of the transmittable/receivable frequency at the application of the direct-current bias voltage having an (n−1)-th bias voltage value, based on the bias voltage-frequency relation information, when n is 2 or more; and applying the direct-current bias voltage having the n-th bias voltage value to the capacitive micromachined ultrasonic transducer belonging to the n-th group.

17. A control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of two groups, each of the two groups including at least one of the capacitive micromachined ultrasonic transducers, the method comprising:

calculating a first bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage;

calculating a second bias voltage value so that a maximum value of the operating frequency is a maximum value of the transmittable/receivable frequency, based on the bias voltage-frequency relation information;

calculating a maximum frequency for determination which is the maximum value of the transmittable/receivable frequency at the application of the direct-current bias voltage having the first bias voltage value, based on the bias voltage-frequency relation information;

calculating a minimum frequency for determination which is the minimum value of the transmittable/receivable frequency at application of the direct-current bias voltage having the second bias voltage value, based on the bias voltage-frequency relation information;

determining whether or not the maximum frequency for determination is more than or equal to the minimum frequency for determination;

resetting the maximum frequency to a smaller value, and repeating the calculating the second bias voltage value, the calculating the maximum frequency for determination, the calculating the minimum frequency for determination, and the determining, when the maximum frequency for determination is not more than or equal to the minimum frequency for determination; and applying the direct-current bias voltage having the first bias voltage value to the capacitive micromachined ultrasonic transducer belonging to one of the two groups, and applying the direct-current bias voltage having the second bias voltage value to the capacitive micromachined ultrasonic transducer belonging to the other of the groups, when the maximum frequency for determination is more than or equal to the minimum frequency for determination.

18. A control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of m (m is a natural number of 2 or more) groups, each of the m groups including at least one of the capacitive micromachined ultrasonic transducers, the method comprising:

calculating a first bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage;

determining a second bias voltage value so that the minimum value of the transmittable/receivable frequency at application of the direct-current bias voltage having the second bias voltage value is less than or equal to a maximum value of the transmittable/receivable frequency at application of the direct-current bias voltage having the first bias voltage value, based on the bias voltage-frequency relation information;

changing a first applied bias voltage value from the second bias voltage value to the first bias voltage value, with an elapse of time during an operation period, the first applied bias voltage value being a value of an n-th applied bias voltage value (n is a natural number of m or less) when n is 1, the n-th applied bias voltage value being the bias voltage value of the direct-current bias voltage to be applied to the capacitive micromachined ultrasonic transducer belonging to an n-th group;

determining the n-th applied bias voltage value so that the minimum value of the transmittable/receivable frequency at application of the direct-current bias voltage having the n-th applied bias voltage value is less than or equal to the maximum value of the transmittable/receivable frequency at application of the direct-current bias voltage having an (n−1)-th applied bias voltage value, based on the bias voltage-frequency relation information, when n is 2 or more; and applying the direct-current bias voltage having the n-th applied bias voltage value to the capacitive micromachined ultrasonic transducer belonging to the n-th group.

19. A control method of an ultrasonic probe device including capacitive micromachined ultrasonic transducers in which a frequency range of transmittable and receivable ultrasonic waves changes in accordance with a bias voltage value of a direct-current bias voltage to be applied, each of the capacitive micromachined ultrasonic transducers belonging to one of two groups, each of the two groups including at least one of the capacitive micromachined ultrasonic transducers, the method comprising:

calculating a maximum bias voltage value so that a minimum value of an operating frequency which is a continuous frequency band transmitted and/or received by the ultrasonic probe device is a minimum value of a transmittable/receivable frequency, based on bias voltage-frequency relation information indicating a relation between the bias voltage value and the transmittable/receivable frequency in a frequency range of the ultrasonic waves transmittable and/or receivable by the capacitive micromachined ultrasonic transducers at application of the direct-current bias voltage;

calculating a minimum bias voltage value so that a maximum value of the operating frequency is a maximum value of the transmittable/receivable frequency, based on the bias voltage-frequency relation information; calculating a first maximum frequency for determination which is the maximum value of the transmittable/receivable frequency at application of the direct-current bias voltage having the maximum bias voltage value, based on the bias voltage-frequency relation information;

calculating a first minimum frequency for determination which is the minimum value of the transmittable/receivable frequency at application of the direct-current bias voltage having the minimum bias voltage value, based on the bias voltage-frequency relation information;

calculating an intermediate bias voltage value so that the first maximum frequency for determination is the maximum value of the transmittable/receivable frequency, based on the bias voltage-frequency relation information;

calculating a second maximum frequency for determination which is the maximum value of the transmittable/receivable frequency at application of the direct-current bias voltage having the intermediate bias voltage value, based on the bias voltage-frequency relation information;

determining whether or not the second maximum frequency for determination is more than or equal to the first minimum frequency for determination;

calculating the bias voltage value so that the first minimum frequency for determination is the maximum value of the transmittable/receivable frequency, and resetting the bias voltage value to the intermediate bias voltage value, based on the bias voltage-frequency relation information, when the second maximum frequency for determination is not more than or equal to the first minimum frequency for determination;

changing a first applied bias voltage value from the intermediate bias voltage value to the maximum bias voltage value with an elapse of time during an operation period;

determining whether or not a third maximum frequency for determination as the maximum value of the transmittable/receivable frequency at application of the direct-current bias voltage having the first applied bias voltage value which is calculated based on the bias voltage-frequency relation information is more than or equal to the first minimum frequency for determination;

applying the direct-current bias voltage having the first applied bias voltage value to the capacitive micromachined ultrasonic transducer belonging to one of the two groups, and applying the direct-current bias voltage having the minimum bias voltage value to the capacitive micromachined ultrasonic transducer belonging to the other the two groups, when the third maximum frequency for determination is more than or equal to the first minimum frequency for determination; and calculating a second applied bias voltage value so that the minimum value of the transmittable/receivable frequency is less than or equal to the third maximum frequency for determination, based on the bias voltage-frequency relation information, applying the direct-current bias voltage having the first applied bias voltage value to the capacitive micromachined ultrasonic transducer belonging to one of the two groups, and applying the direct-current bias voltage having the second applied bias voltage value to the capacitive micromachined ultrasonic transducer belonging to the other of the two groups, when the third maximum frequency for determination is not more than or equal to the first minimum frequency for determination.

20. The control method of the ultrasonic probe device according to claim 16, wherein the bias voltage-frequency relation information includes information that a relation between the bias voltage value and the minimum value of the transmittable/receivable frequency indicates a relation between the bias voltage value and a resonance frequency of the capacitive micromachined ultrasonic transducer, and information that a relation between the bias voltage value and the maximum value of the transmittable/receivable frequency indicates a relation between the bias voltage value and an antiresonant frequency of the capacitive micromachined ultrasonic transducer.

21. The control method of the ultrasonic probe device according to claim 16, further comprising: Determining the minimum value of the operating frequency from a reaching distance of the ultrasonic wave which is designated by a user, based on a relation between the reaching distance of the ultrasonic wave and a frequency of the ultrasonic wave.

22. A method for controlling an ultrasonic probe device comprising a plurality of ultrasonic transducers, wherein each of the plurality of ultrasonic transducers is configured to transmit and/or receive ultrasonic waves in a frequency range that varies with a bias voltage value of a bias voltage applied to the each of the plurality of ultrasonic transducers, the method comprising:

performing a determination function to determine the bias voltage value of the bias voltage to be applied to the each of the plurality of ultrasonic transducers during an operation period of the plurality of ultrasonic transducers such that a predetermined continuous frequency band is covered by a combination of the frequency ranges of the transmitted and/or received ultrasonic waves from the plurality of ultrasonic transducers, wherein the determination function comprises determining:
a first bias voltage value of a first bias voltage to be applied to a first ultrasonic transducer of the plurality of ultrasonic transducers such that the first ultrasonic transducer transmits and/or received ultrasonic waves in a first frequency range, and
a second bias voltage value of a second bias voltage to be applied to a second ultrasonic transducer of the plurality of ultrasonic transducers such that the second ultrasonic transducer transmits and/or receives ultrasonic waves in second frequency range, at least a part of the second frequency range being different from the first frequency range.

23. The ultrasonic probe device according to claim 1, wherein the determination function comprises determining at least a part of the first frequency range being different from the second frequency range.

24. The method for controlling an ultrasonic probe device according to claim 22, wherein the determination function comprises determining at least a part of the first frequency range being different from the second frequency range.

25. The ultrasonic probe device according to claim 3, wherein the number of groups of the plurality of ultrasonic transducers is m (m is a natural number of 2 or more), the band control unit includes: a bias voltage calculation section configured to calculate an n-th bias voltage value (n is a natural number of m or less) based on the bias voltage-frequency relation information; and a frequency calculation section configured to calculate an n-th maximum frequency for determination based on the bias voltage-frequency relation information, and wherein the bias voltage calculation section calculates the n-th bias voltage value so that a minimum value of the operating frequency is a minimum value of the transmittable/receivable frequency, when n is 1, and calculates the n-th bias voltage value so that an (n−1)-th maximum frequency for determination is more than or equal to a minimum value of the transmittable/receivable frequency, when n is 2 or more, the frequency calculation section calculates the n-th maximum frequency for determination which is a maximum value of the transmittable/receivable frequency at application of the direct-current bias voltage having the n-th bias voltage value, when n is more than or equal to 1 and less than or equal to (m−1), and the bias voltage change unit is configured to apply the direct-current bias voltage having the n-th bias voltage value to the capacitive micromachined ultrasonic transducer belonging to the n-th group.

26. The ultrasonic probe device according to claim 11, wherein the number of groups of the plurality of ultrasonic transducers is two, the band control unit includes: a bias voltage calculation section configured to calculate a maximum bias voltage value so that a minimum value of the operating frequency is a minimum value of the transmittable/receivable frequency, and a minimum bias voltage value so that a maximum value of the operating frequency is a maximum value of the transmittable/receivable frequency, based on the bias voltage-frequency relation information; a frequency calculation section configured to calculate a first maximum frequency for determination which is the maximum value of the transmittable/receivable frequency at application of the direct-current bias voltage having the maximum bias voltage value, and a first minimum frequency for determination which is the minimum value of the transmittable/receivable frequency at application of the direct-current bias voltage having the minimum bias voltage value, based on the bias voltage-frequency relation information; an intermediate frequency calculation section configured to calculate an intermediate bias voltage value so that the first maximum frequency for determination is the maximum value of the transmittable/receivable frequency, and a second maximum frequency for determination which is the maximum value of the transmittable/receivable frequency at application of the direct-current bias voltage having the intermediate bias voltage value, based on the bias voltage-frequency relation information; a frequency determination section configured to determine whether or not the second maximum frequency for determination is more than or equal to the first minimum frequency for determination; a frequency resetting section configured to calculate the bias voltage value so that the first minimum frequency for determination is the maximum value of the transmittable/receivable frequency, and resets the bias voltage value to the intermediate bias voltage value, based on the bias voltage-frequency relation information, when the second maximum frequency for determination is not more than or equal to the first minimum frequency for determination; and a bias voltage determination section configured to determine a first applied bias voltage value as the bias voltage value of the direct-current bias voltage to be applied to the capacitive micromachined ultrasonic transducer belonging to one of the two groups, and a second applied bias voltage value as the bias voltage value of the direct-current bias voltage to be applied to the capacitive micromachined ultrasonic transducer belonging to the other of the two groups, and wherein the bias voltage determination section is configured to change the first applied bias voltage value from the intermediate bias voltage value to the maximum bias voltage value with the elapse of time during the operation period, the frequency calculation section is configured to calculate a third maximum frequency for determination which is the maximum value of the transmittable/receivable frequency at application of the direct-current bias voltage having the first applied bias voltage value, based on the bias voltage-frequency relation information, the frequency determination section is configured to determine whether or not the third maximum frequency for determination is more than or equal to the first minimum frequency for determination, when the third maximum frequency for determination is more than or equal to the first minimum frequency for determination, the bias voltage change unit applies the direct-current bias voltage having the first applied bias voltage value to the capacitive micromachined ultrasonic transducer belonging to one of the two groups, and applies the direct-current bias voltage having the minimum bias voltage value to the capacitive micromachined ultrasonic transducer belonging to the other of the two groups, and when the third maximum frequency for determination is not more than or equal to the first minimum frequency for determination, the bias voltage determination section calculates the second applied bias voltage value so that the minimum value of the transmittable/receivable frequency is less than or equal to the third maximum frequency for determination, based on the bias voltage-frequency relation information, and the bias voltage change unit applies the direct-current bias voltage having the first applied bias voltage value to the capacitive micromachined ultrasonic transducer belonging to one of the two groups, and applies the direct-current bias voltage having the second applied bias voltage value to the capacitive micromachined ultrasonic transducer belonging to the other of the two groups.

27. The ultrasonic probe device according to claim 11, wherein the number of groups of the plurality of ultrasonic transducers is m (m is a natural number of 2 or more), the band control unit includes: a bias voltage calculation section configured to calculate a first bias voltage value so that a minimum value of the operating frequency is a minimum value of the transmittable/receivable frequency, based on the bias voltage-frequency relation information; a frequency calculation section configured to calculate a maximum value of the transmittable/receivable frequency at application of the direct-current bias voltage having the first bias voltage value, based on the bias voltage-frequency relation information; and a bias voltage determination section configured to determine the bias voltage value to be applied to the capacitive micromachined ultrasonic transducers during the operation period, and wherein the bias voltage determination section is configured to change a first applied bias voltage value from the second bias voltage value to the first bias voltage value, the first applied bias voltage value being a value of an n-th applied bias voltage value (n is a natural number of m or less) when n is 1, the n-th applied bias voltage value being the bias voltage value of the direct-current bias voltage to be applied to the capacitive micromachined ultrasonic transducer belonging to an n-th group, the frequency calculation section is configured to calculate an n-th maximum frequency for determination which is the maximum value of the transmittable/receivable frequency at application of the direct-current bias voltage having the n-th bias voltage value, when n is 2 or more and (m−1) or less, the bias voltage determination section is configured to determine an n-th applied bias voltage value so that the minimum value of the transmittable/receivable frequency at the application of the direct-current bias voltage having the n-th applied bias voltage value is less than or equal to an (n−1)-th maximum frequency for determination, based on the bias voltage-frequency relation information, when n is 2 or more, and the bias voltage change unit is configured to change, to the n−th applied bias voltage value, the bias voltage value of the direct-current bias voltage to be applied to the capacitive micromachined ultrasonic transducer belonging to the n−th group.

28. The ultrasonic probe device according to claim 1, wherein the ultrasonic probe device transmits the ultrasonic wave at a start of the operation period, and the ultrasonic probe device receives the ultrasonic wave during the operation period, the band control unit is configured to change the bias voltage value during the operation period to receive the ultrasonic wave, the ultrasonic probe device further comprising a storage unit which stores bias voltage-frequency relation information indicating a relation between the bias voltage value and a transmittable/receivable frequency in a frequency range of the ultrasonic waves transmittable and/or receivable by the capacitive micromachined ultrasonic transducers at application of the direct-current bias voltage, the number of groups of the plurality of ultrasonic transducers is two, the band control unit includes: a bias voltage calculation section configured to calculate a maximum bias voltage value so that a minimum value of the operating frequency is a minimum value of the transmittable/receivable frequency, and a minimum bias voltage value so that a maximum value of the operating frequency is a maximum value of the transmittable/receivable frequency, based on the bias voltage-frequency relation information; a frequency calculation section configured to calculate a first maximum frequency for determination which is the maximum value of the transmittable/receivable frequency at application of the direct-current bias voltage having the maximum bias voltage value, and a first minimum frequency for determination which is the minimum value of the transmittable/receivable frequency at application of the direct-current bias voltage having the minimum bias voltage value, based on the bias voltage-frequency relation information; an intermediate frequency calculation section configured to calculate an intermediate bias voltage value so that the first maximum frequency for determination is the maximum value of the transmittable/receivable frequency, and a second maximum frequency for determination which is the maximum value of the transmittable/receivable frequency at the application of the direct-current bias voltage having the intermediate bias voltage value, based on the bias voltage-frequency relation information; a frequency determination section configured to determine whether or not the second maximum frequency for determination is more than or equal to the first minimum frequency for determination; a frequency resetting section configured to calculate the bias voltage value so that the first minimum frequency for determination is the maximum value of the transmittable/receivable frequency, and resets the bias voltage value to the intermediate bias voltage value, based on the bias voltage-frequency relation information, when the second maximum frequency for determination is not more than or equal to the first minimum frequency for determination; and a bias voltage determination section configured to determine a first applied bias voltage value which is the bias voltage value of the direct-current bias voltage to be applied to the capacitive micromachined ultrasonic transducer belonging to one of the two groups, and a second applied bias voltage value which is the bias voltage value of the direct-current bias voltage to be applied to the capacitive micromachined ultrasonic transducer belonging to the other of the two groups, and wherein the bias voltage determination section, with an elapse of time during the operation period, is configured to change the first applied bias voltage value from the intermediate bias voltage value to the maximum bias voltage value, and maintain the second applied bias voltage value at the minimum bias voltage value, and maintain the first applied bias voltage value at the maximum bias voltage value, and change the second applied bias voltage value from the minimum bias voltage value to the intermediate bias voltage value, after changing the first applied bias voltage value to the maximum bias voltage value, and the bias voltage change unit is configured to apply the direct-current bias voltage having the first applied bias voltage value to the capacitive micromachined ultrasonic transducer belonging to one of the two groups, and apply the direct-current bias voltage having the second applied bias voltage value to the capacitive micromachined ultrasonic transducer belonging to the other of the two groups.

* * * * *